United States Patent [19]

Knippscheer et al.

[11] Patent Number: 5,125,240

[45] Date of Patent: Jun. 30, 1992

[54] STORAGE APPARATUS, PARTICULARLY WITH AUTOMATIC INSERTION AND RETRIEVAL

[75] Inventors: Hermann Knippscheer, Baldwin, N.Y.; Daniel D. Richard, Sedona, Ariz.

[73] Assignee: Cryo-Cell International, Inc., Baldwin, N.Y.

[21] Appl. No.: 660,736

[22] Filed: Feb. 22, 1991

Related U.S. Application Data

[60] Division of Ser. No. 482,239, Feb. 20, 1990, Pat. No. 5,022,236, which is a division of Ser. No. 389,543, Aug. 4, 1989, Pat. No. 4,969,336, and a continuation-in-part of Ser. No. 455,170, Dec. 22, 1989.

[51] Int. Cl.$^5$ ............................................. F25D 23/02
[52] U.S. Cl. ...................................... 62/266; 62/336; 62/337; 62/440; 414/331
[58] Field of Search ................. 62/266, 440, 448, 336, 62/337; 414/331

[56] References Cited

U.S. PATENT DOCUMENTS

| | | | |
|---|---|---|---|
| 1,938,985 | 12/1933 | Starr | 62/37 |
| 2,599,173 | 6/1952 | Hamilton | 62/336 |
| 2,928,705 | 3/1960 | Goldsmith | 312/305 |
| 2,950,605 | 8/1960 | Hennion | 312/268 |
| 3,034,845 | 5/1962 | Haumann | 312/268 |
| 3,100,969 | 8/1963 | Elfving | 62/3 |
| 3,141,123 | 7/1964 | Olson | 312/268 |
| 3,227,501 | 1/1966 | Austin et al. | 312/97 |
| 3,327,833 | 6/1967 | Jungner et al. | 198/19 |
| 3,564,727 | 2/1971 | Fraser | 62/333 |
| 3,583,171 | 6/1971 | Flynn et al. | 62/266 |
| 3,696,631 | 10/1972 | Valdes | 62/282 |
| 3,942,334 | 3/1976 | Pink | 62/266 |
| 4,124,992 | 11/1978 | Chimel | 62/74 |
| 4,199,022 | 4/1980 | Senkan et al. | 165/2 |
| 4,304,293 | 12/1981 | Scheiwe et al. | 62/62 |
| 4,314,459 | 2/1982 | Rivoire | 62/514 R |
| 4,340,263 | 7/1982 | Webb | 62/268 |
| 4,480,682 | 11/1984 | Kaneta et al. | 165/14 |
| 4,531,373 | 6/1985 | Rubinsky | 62/63 |
| 4,627,799 | 12/1986 | Terauchi | 418/55 |
| 4,681,839 | 7/1987 | Swartz | 435/1 |
| 4,712,607 | 12/1987 | Lindemans et al. | 165/30 |
| 4,713,941 | 12/1987 | Toyoda et al. | 62/50 |
| 4,722,058 | 1/1988 | Nakayama et al. | 364/479 |
| 4,790,141 | 12/1988 | Glascock | 62/78 |
| 4,818,169 | 4/1989 | Schram | 414/331 |
| 4,848,537 | 7/1989 | Richards et al. | 414/331 |
| 4,870,829 | 3/1989 | Oullette | 62/51.1 |

FOREIGN PATENT DOCUMENTS 2509762 9/1976 Fed. Rep. of Germany.

Primary Examiner—Ronald C. Capossela
Attorney, Agent, or Firm—R. Neil Sudol; Henry D. Coleman

[57] ABSTRACT

A cryogenic storage apparatus comprises a housing with an automatically operated access door. A holder device disposed in the housing supports a plurality of specimen-containing ampules, while a conveyor moves the holder device, together with the plurality of ampules, through cooling fluid in the housing along a path preferably including a snaking portion with vertically extending folds. An inverted L-shaped cooling component with an opened upper side is disposed in the housing for maintaining the cooling fluid at a predetermined low temperature. An extraction mechanism disposed outside of the housing at the access door serves to remove a selectable ampule positioned in the housing in juxtaposition to the door. A tracking device automatically tracks the positions of the ampules during motion thereof along the snaking path, while a control unit connected to the tracking device, the drive mechanism, the conveyor and the extraction mechanism activates the conveyor to move a given ampule along the path to the access door, opens the access door, and operates the extraction mechanism to remove the given ampule from the holder device and out through the opened door.

29 Claims, 17 Drawing Sheets

STORAGE APPARATUS, PARTICULARLY WITH AUTOMATIC INSERTION AND RETRIEVAL

CROSS-REFERENCE TO RELATED APPLICATION

This application is a divisional of commonly owned U.S. patent application Ser. No. 482,239 filed Feb. 20, 1990, now U.S. Pat. No. 5,022,236, which is a divisional of commonly owned U.S. patent application Ser. No. 389,543 filed Aug. 4, 1989, now U.S. Pat. No. 4,969,336 and a continuation-in-part of commonly owned U.S. patent application Ser. No. 455,170 filed Dec. 22, 1989.

BACKGROUND OF THE INVENTION

This invention relates to a storage apparatus. More particularly, this invention relates to an apparatus with automatic insertion and retrieval of samples from a storage container. More specifically, this invention relates to an apparatus for the preservation of biological specimens at various temperatures, including but not limited to the temperature of liquid nitrogen.

When properly treated, biological specimens can be stored almost indefinitely at temperatures approaching that of liquid nitrogen so long as that temperature is maintained. However, once the temperature of a specimen is raised, especially to a level where thawing occurs, the integrity of the specimen suffers if the specimen is then refrozen. Conventional devices for storing biological specimens at low temperatures are adequate for the storage of a group of samples, but if one or more sample are removed from the group, other samples may be exposed to thawing temperatures, with a resultant decrease in the viability of the refrozen cells.

In some circumstances, however, it may be desirable to retain the ability to retrieve several samples simultaneously, for example, in groups.

OBJECTS OF THE INVENTION

An object of the present invention is to provide a storage apparatus wherein specimen-containing vials may be recovered or retrieved one at a time or in multiples, either automatically or manually.

Another object of the present invention is to provide a storage system with cross-checks for ensuring proper retrieval of requested samples.

A further object of the present invention is to provide a storage system with means for efficiently and quickly removing all of the specimen-containing receptacles from a storage unit in case of malfunction of that unit.

A more specific object of the present invention is to provide a storage apparatus wherein specimens are maintained at a substantially constant temperature, particularly a low temperature at or near the temperature of liquid nitrogen.

Another specific object of the present invention is to provide such an apparatus wherein exposure of the specimens to temperatures above that of liquid nitrogen, especially thawing temperatures, is prevented.

SUMMARY OF THE INVENTION

A storage apparatus in accordance with the present invention comprises a housing defining a storage chamber, an insertion and removal mechanism operatively connected to the housing for alternately inserting and removing specimen-containing receptacles from the storage chamber, and a control unit operatively connected to the insertion and removal mechanism for automatically tracking the locations of specimen-containing receptacles in the housing and for controlling the insertion and removal of specimen-containing receptacles from the storage chamber.

Pursuant to features of the present invention, the housing has an access door and a component such as a drive is operatively connected to the door for alternately opening and closing the door. The control unit further includes an extraction mechanism disposed outside of the housing at the door for removing a selectable one of the receptacles positioned in the storage chamber in juxtaposition to the door.

Pursuant to further features of the present invention, holders are provided in the storage chamber for supporting a plurality of specimen-containing receptacles and a conveyor is provided for moving the holders, together with the plurality of receptacles, in the storage chamber along a predetermined path in the storage chamber. The predetermined path advantageously includes a snaking portion with a plurality of vertically extending folds and further includes a segment juxtaposed to the door.

In accordance with a particular feature of the present invention, a transfer mechanism is operatively connectable to the housing and the conveyor for removing all of the specimen-containing receptacles in a single operation from the storage chamber into another storage apparatus.

A storage apparatus in accordance with the invention may also comprise a selector such as a keyboard operatively connected to the control unit and disposed outside of the housing for enabling a selection of one of the receptacles by an operator.

A storage system in accordance with the invention comprises a plurality of storage facilities each including:

(a) a housing defining a storage chamber;

(b) an insertion and removal mechanism operatively connected to the housing for alternately inserting and removing specimen-containing receptacles from the storage chamber; and (c) a local control unit at the same location as the housing and operatively connected to the insertion and removal mechanism for automatically tracking the locations of specimen-containing receptacles in the housing and for controlling the insertion and removal of specimen-containing receptacles from the storage chamber. A remote control unit is operatively connected to the local control unit of each of the storage facilities for monitoring the operations thereof and for cross-checking identities of duplicate specimen-containing receptacles in different ones of the storage facilities.

Each of the storage facilities advantageously includes a verification device at the respective housing for automatically verifying that the correct receptacle has been retrieved under the control of the respective local control unit, the remote control unit having means connected to the local control unit of each of the storage facilities for receiving verification of a retrieved receptacle and for comparing identities of receptacles retrieved substantially simultaneously at different ones of the storage facilities. The verification device preferably includes a laser reader for scanning bar codes attached to the receptacles.

Another storage system in accordance with the present invention comprises a pair of storage facilities each including:

(a) a housing defining a storage chamber;

(b) an insertion and removal mechanism operatively connected to the housing for alternately inserting and removing specimen-containing receptacles from the storage chamber; and (c) a local control unit at the same location as the housing and operatively connected to the insertion and removal mechanism for automatically tracking the locations of specimen-containing receptacles in the housing and for controlling the insertion an removal of specimen-containing receptacles from the storage chamber. A receptacle transfer apparatus is operatively connected to the housing of each of the storage facilities and to the conveyor of each of the storage facilities for removing all of the specimen-containing receptacles in a single operation from the storage chamber of one of the storage facilities into the storage chamber of the other of the storage facilities.

Pursuant to a specific feature of the present invention, each of the storage facilities further comprises holders or support elements in the respective storage chamber for supporting a plurality of specimen-containing receptacles and a conveyor for moving the holders, together with the plurality of receptacles, in the storage chamber along a predetermined path.

Another apparatus in accordance with the present invention is provided for transferring specimen-containing receptacles from a first storage unit to a second storage unit, wherein each of the storage units includes a respective housing and specimen conveyor in the housing for holding a multiplicity of the specimen-containing receptacles and moving the receptacles within the housing. Such a transfer apparatus comprises a transfer housing, a closure component for connecting that housing to the housing of each of the storage units so that the transfer housing communicates in an essentially air tight manner with the housing of each of the storage units. A transfer conveyor is operatively connectable to the conveyor of each of the storage units for moving receptacles from one of the storage units to the other of the storage units. A drive is operatively connected to the transfer conveyor for moving the receptacles from the one storage unit to the other.

According to a specific feature of this embodiment of the invention, the conveyor includes a pair of flexible endless elements extending along the path and the holder or support elements include a plurality of bar members pivotably connected to and extending between the endless elements.

A storage apparatus in accordance with a particular embodiment of the present invention comprises (a) a housing defining a storage chamber with an access door, (b) a component operatively connected to the door for alternately opening and closing the door, (c) holders or support elements in the storage chamber for supporting a plurality of specimen-containing receptacles, (d) a conveyor for moving the holders, together with the plurality of receptacles, in the storage chamber along a predetermined path including a segment juxtaposed to the door, and (e) an extraction mechanism disposed outside of the housing at the door for removing a selectable one of the receptacles positioned in the storage chamber in juxtaposition to the door.

The extraction mechanism advantageously includes a carriage member movably mounted to the housing, a first linear drive for moving the carriage member, a component for securing a hold on a selected on of the receptacles positioned in the storage chamber in juxtaposition to the door, and second linear drive connected to the holding component for moving the holding component along a substantially linear path through the door.

Pursuant to a specific feature of the present invention, the extraction mechanism further includes (a) a housing portion rotatably mounted to the carriage member, the second linear means being at least partially mounted to the housing, and (b) rotary mean operatively connected to the housing portion for rotating same relative to the carriage member.

Pursuant to yet another feature of the present invention, the storage apparatus further comprises a tracking mechanism operatively connected to the conveyor for automatically tracking the positions of the plurality of receptacles during motion thereof along the path under action of the conveyor, a selector outside of the housing for enabling a selection of one of the receptacles by an operator, and a control unit operatively connected to the selector, the tracking mechanism, the conveyor and the extraction mechanism for operating the conveyor, upon selection of a given one of the receptacles via the selector, to move the given receptacle along the path to the door, for opening the door, and for operating the extraction mechanism to remove the given one of the receptacles from the holding component and out through the opened door.

Pursuant to another feature of the present invention, an enclosure is provided outside of the housing and the extraction mechanism removes a receptacle from the storage chamber and inserts the removed receptacle into the enclosure. The enclosure is preferably attached to the housing.

Pursuant to yet another feature of the invention, a verification device is disposed at the door of the storage chamber for automatically verifying that the correct receptacle has been retrieved by the extraction mechanism. The verification device preferably includes a laser reader for scanning bar codes attached to the receptacles.

DETAILED DESCRIPTION

Figure 1:
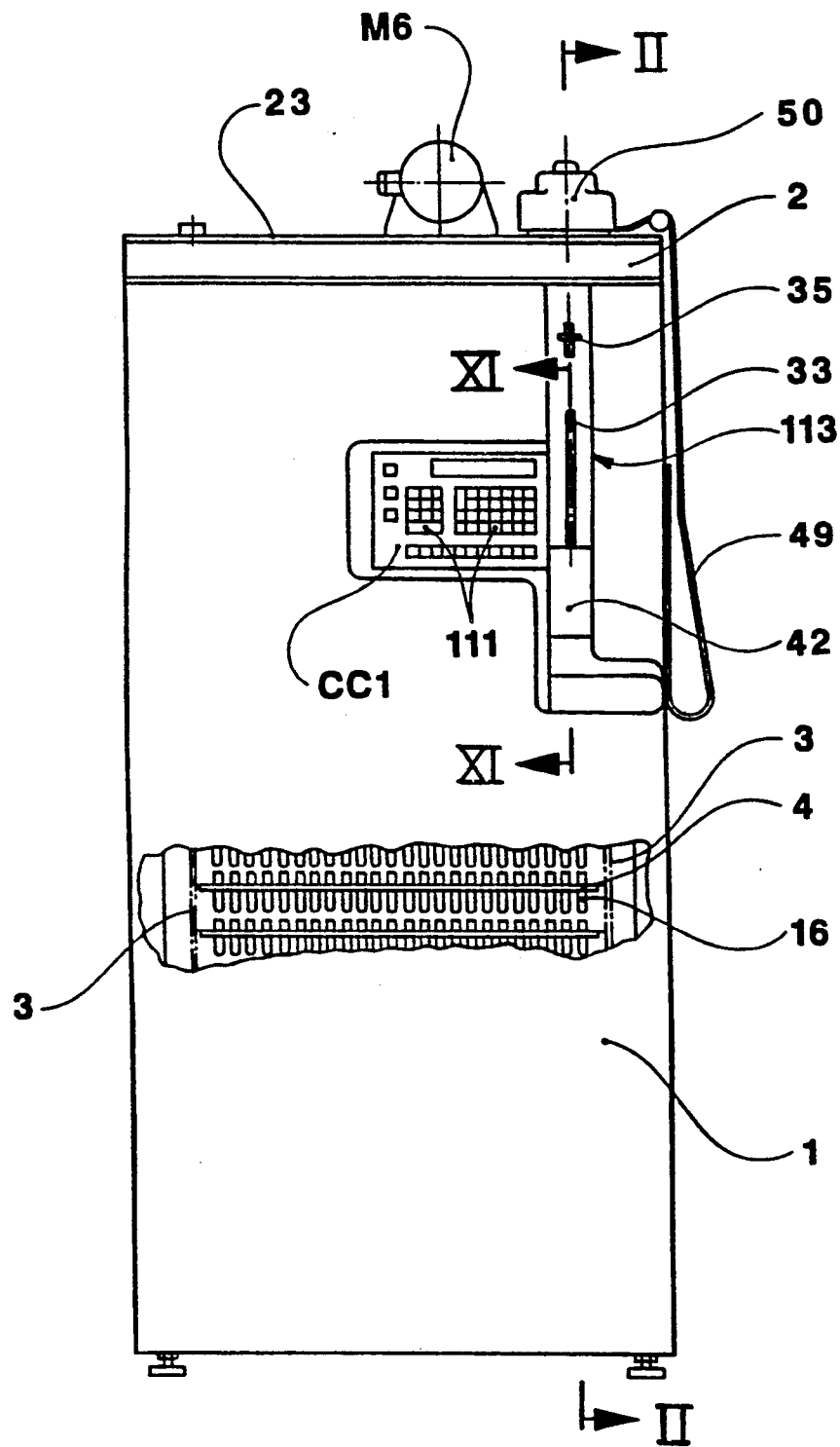
FIG. 1 is a front elevational view of a cryogenic storage apparatus in accordance with the present invention.
Figure 2:
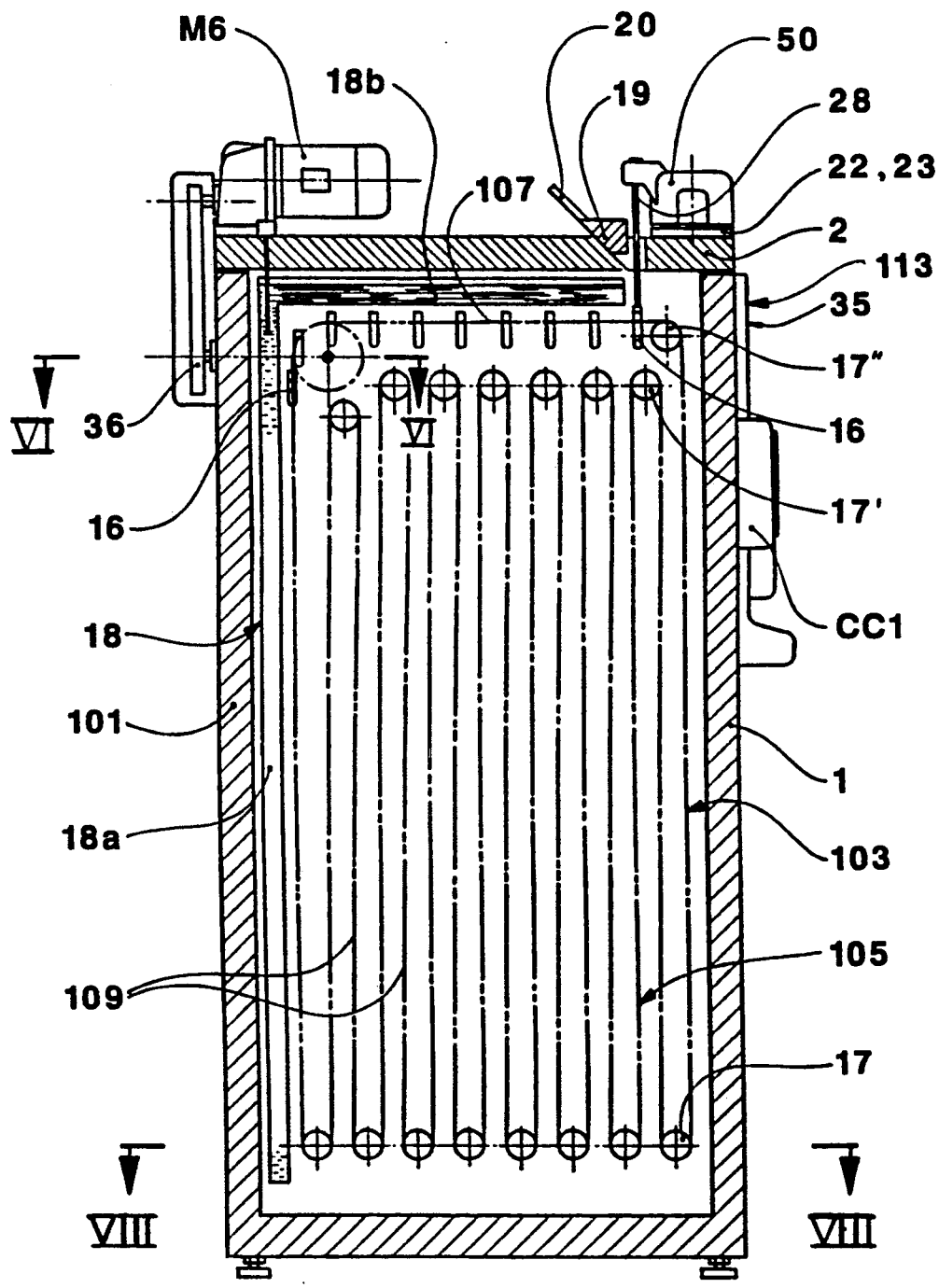
FIG. 2 is a schematic cross-sectional view taken along line A—A in FIG. 1.

As illustrated in FIGS. 1 and 2, a cryogenic storage apparatus for maintaining ampules or receptacles 16 at a substantially uniform low temperature approximately at the temperature of liquid nitrogen comprises a housing 1 with a lid or cover 2.

Ampules 16 are loaded into and retrieved from housing 1 automatically under the control of a microprocessor or computer CC1 mounted to housing 1 on a side wall thereof. The insertion and withdrawal of individual ampules is accomplished without exposure of the other specimen-containing ampules in housing 1 to ambient room-temperature air.

The cryogenic storage apparatus illustrated in FIGS. 1 and 2 will store approximately 8,000 ampules, each containing a respective specimen or sample.

Housing 1 defines a prismatic storage chamber which can be partially or totally filled with liquid nitrogen or a low-temperature gas. In the latter case, the gas is maintained at a low temperature by a minimal amount of liquid nitrogen held in a specially designed container 18 (FIG. 2). Container 18 preferably has an L-shaped cross-section with vertically extending leg 18a and a horizontally oriented leg 18b communicating with one another. Vertical leg 18a extends parallel and proximate to a side wall 101 of housing 1, while horizontal leg 18b is disposed near cover or upper wall 2 of the housing. Vertical leg 18a is provided on one side with a multiplicity of cooling fins which may engage side wall 101, while horizontal leg 18b is open along an upper side. The shape and location of container 18 are designed to achieve a temperature balance within housing 1 by virtue of radiant and gravitational cooling.

It is to be noted that container 18 may have a modified form which nevertheless provides the advantages of the L-shape shown in the drawings. For example, container 18 may be U-shaped, with a pair of legs extending down the sides of housing a and with the bight of the U extending parallel to the upper wall of the housing. In both of these specific configurations, L-shaped or U-shaped, the upper portion of the coolant container is open to facilitate vaporization of the coolant. In the case of a U-shaped coolant container, an opening may be provided in the base to permit the insertion and removal of sample containing ampule.

Figure 3:
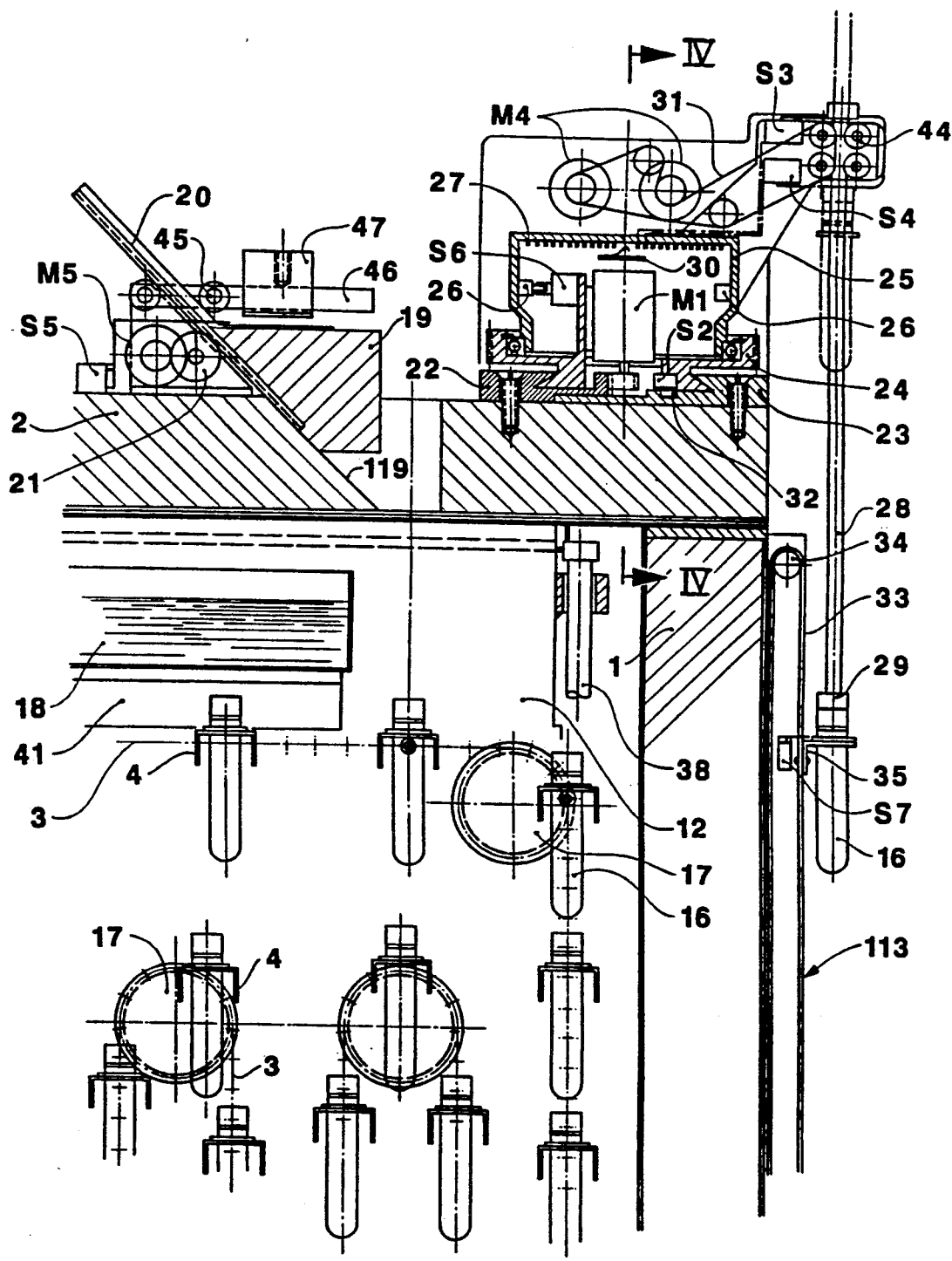
FIG. 3 is an enlarged, detail view ("Detail A") of the upper right hand corner of FIG. 2.

As shown in FIGS. 1 and 3, pluralities of ampules 16 are held on respective support bars 4 extending between and pivotably connected at their ends to a pair of endless conveyor chains 3. As shown in FIG. 2, chains 3 define a travel path 103 for the ampules through the housing chamber, the travel path having a lower snaking portion 105 and an upper portion 107 extending horizontally parallel to cover 2. Snaking portion 105 includes a plurality of vertically extending folds 109.

The position of each ampule 16 along path 10 is tracked in part by computer CC1. The computer memorizes the positions of all the ampules and updates the positions continuously during the motion of conveyor chains 3. In response to a selection made by an operator via a keyboard 111 (FIG. 1) of computer CC1, the computer controls the movement of chains 3 to position the selected ampule directly below an access door 19 in cover 2 (see FIGS. 2 and 3).

The snake-like alternating up and down movements of bars 4 and ampules 16 supported thereby contributes to the achievement of a gravitational temperature balance throughout the storage unit, in the case that coolant container 18 is being utilized.

The processes and devices for storing the liquid nitrogen outside housing 1, feeding it to container 18 and insulating housing 1 are well known in the art and are not further described herein.

The material of housing 1, container 18 and other components of the cryogenic storage apparatus in accordance with the present invention if not specifically set forth elsewhere herein, is preferably stainless steel or another substance suitable for long-term exposure to liquid nitrogen.

As illustrated in FIGS. 1-3, 11 and 12, the cryogenic storage apparatus is provided with an ampule lifting device 113 comprising a conveyor belt 33, pulleys 34 and motors M3 and their supports. The lifting device is particularly advantageous in the case that the height of housing 1 is so great that the ampule, when resting with an insulated enclosure or intermediate storage unit 142, is not easily accessible by an ampule insertion and extraction or retrieval mechanism 50 disposed on cover 2.

Motors M1 through M5 are duplex drives, each working motor being paired with an auxiliary back-up motor as a safety or precautionary measure. In the event that a primary, working motor should fail, the auxiliary motor will take over automatically and an audio visual signal will be generated, alerting an operator to initiate immediate maintenance and repair procedures.

Figure 5:
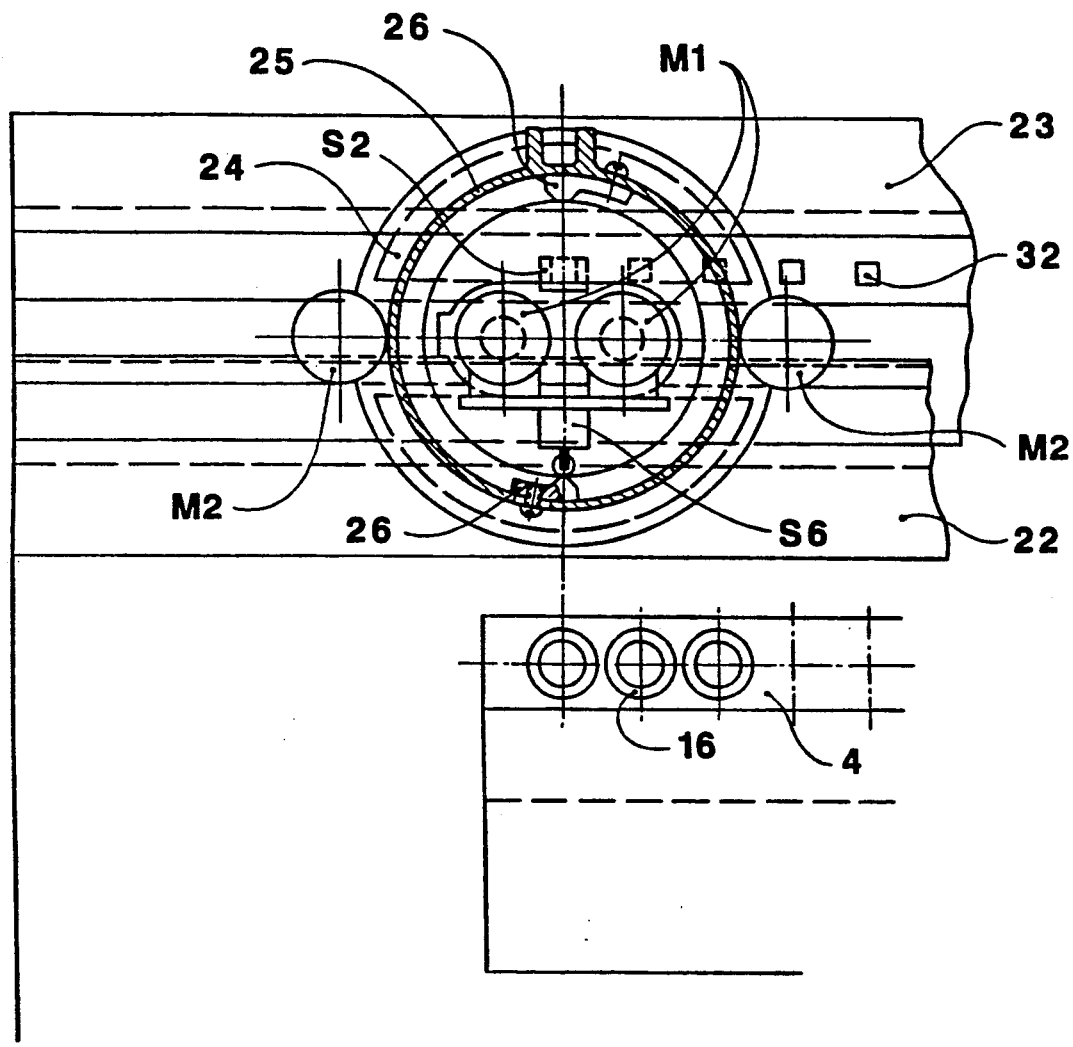
FIG. 5 is a partial cross-sectional view taken along line C—C in FIG. 4.

As illustrated in FIG. 3, support bars 4 have U-shaped transverse cross-sections. As best seen in FIGS. 1, 5 and 7, ampules 16 rest side by side on bars 4. Endless conveyor chains 3 are driven by a chain drive mechanism 115 (FIGS. 6 and 7) including sprockets 5 (FIG. 6) and 6 (FIG. 7) over idler pulleys 17 (FIGS. 3, 8 and 9) absolutely simultaneously along path 103 at a very low speed through the housing chamber. Bars 4 are fastened to chains 3 at spaced locations distanced to enable a free movement and vertical self-alignment of the bars and the ampules held thereby.

Figure 6:
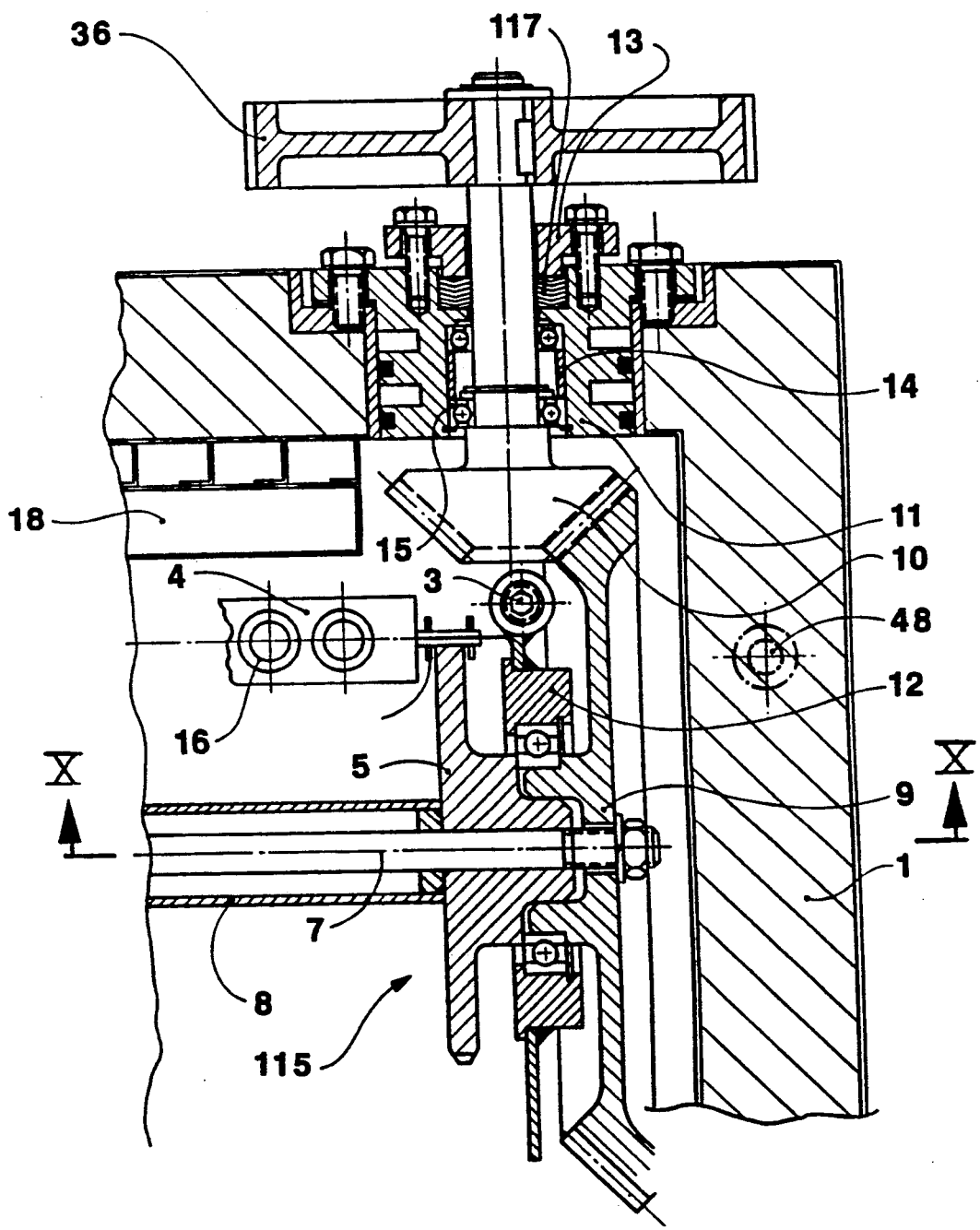
FIG. 6 is a cross-sectional view taken along line D—D in FIG. 2, showing a chain drive gear assembly.
Figure 7:
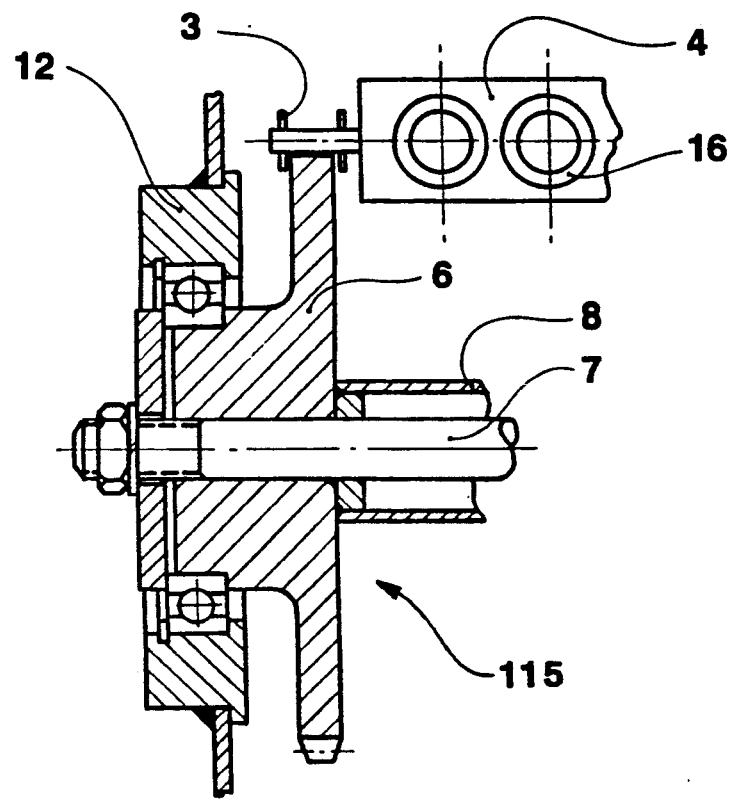
FIG. 7 is a cross-sectional view of a driving gear opposite a gear shown in FIG. 6.
Figure 10:
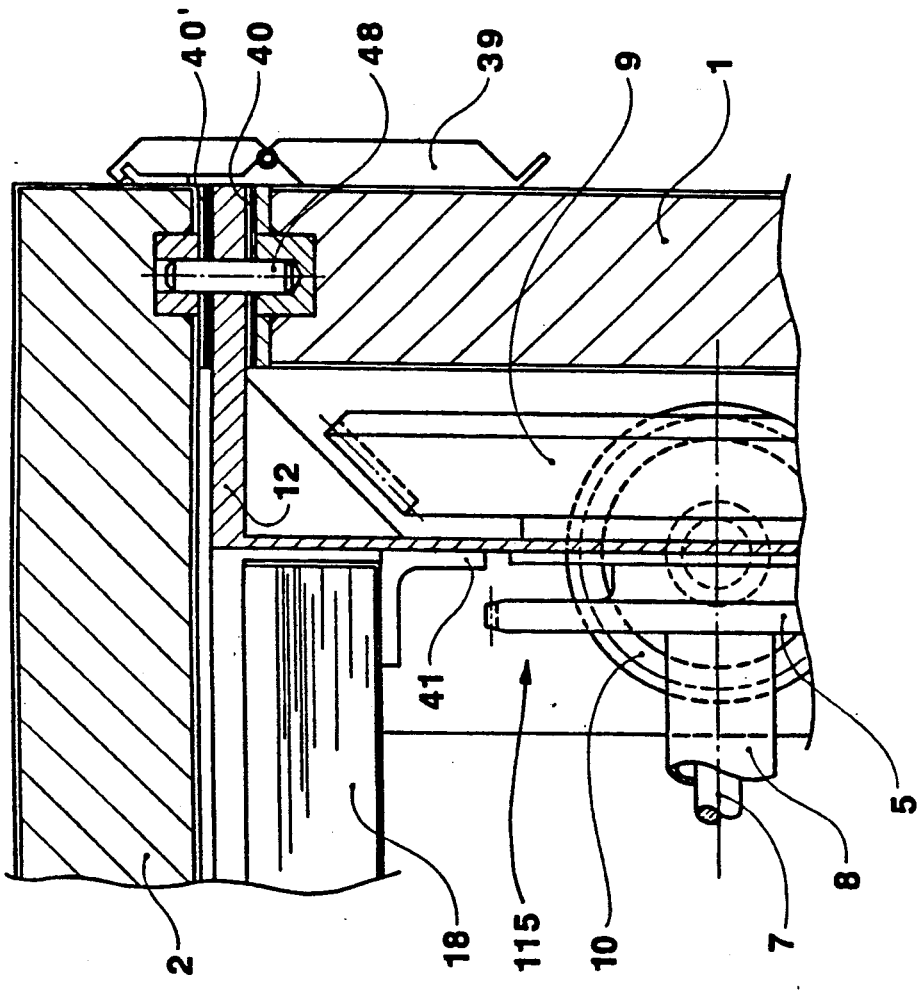
FIG. 10 is a partial cross-sectional view taken along line H—H in FIG. 6.

As depicted in FIGS. 6, 7 and 10, sprockets 5 and 6 of chain drive mechanism 115 are tightened against a spacer 8 by a spindle 7 and are driven by bevel gears 9 and 10. Bevel gear 10 is rotatably supported via roller bearings 15 and a distance sleeve 14 in a bearing casing 11. Driving mechanism 115 is sealed by a stuffing box 13 with graphite packing 117. The bevel gear assembly illustrated in FIG. 6 is designed to be removed an maintained easily and quickly.

Bevel gears 9 and 10 of driving mechanism 115 are powered by a motor M6 disposed on the top and rear portion of cover 2. Motor M6 is operatively connected to bevel gears 9 and 10 via a toothed belt drive 36 (FIGS. 2 and 6).

Figure 8:
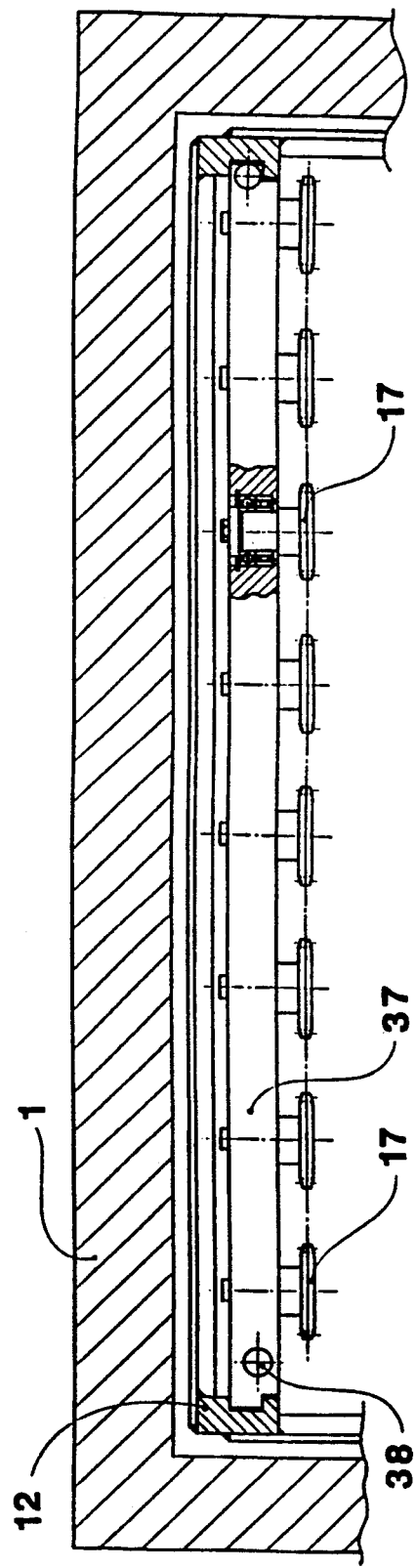
FIG. 8 is a partial cross-sectional view taken along line E—E in FIG. 2, illustrating a chain tensioning mechanism.
Figure 9:
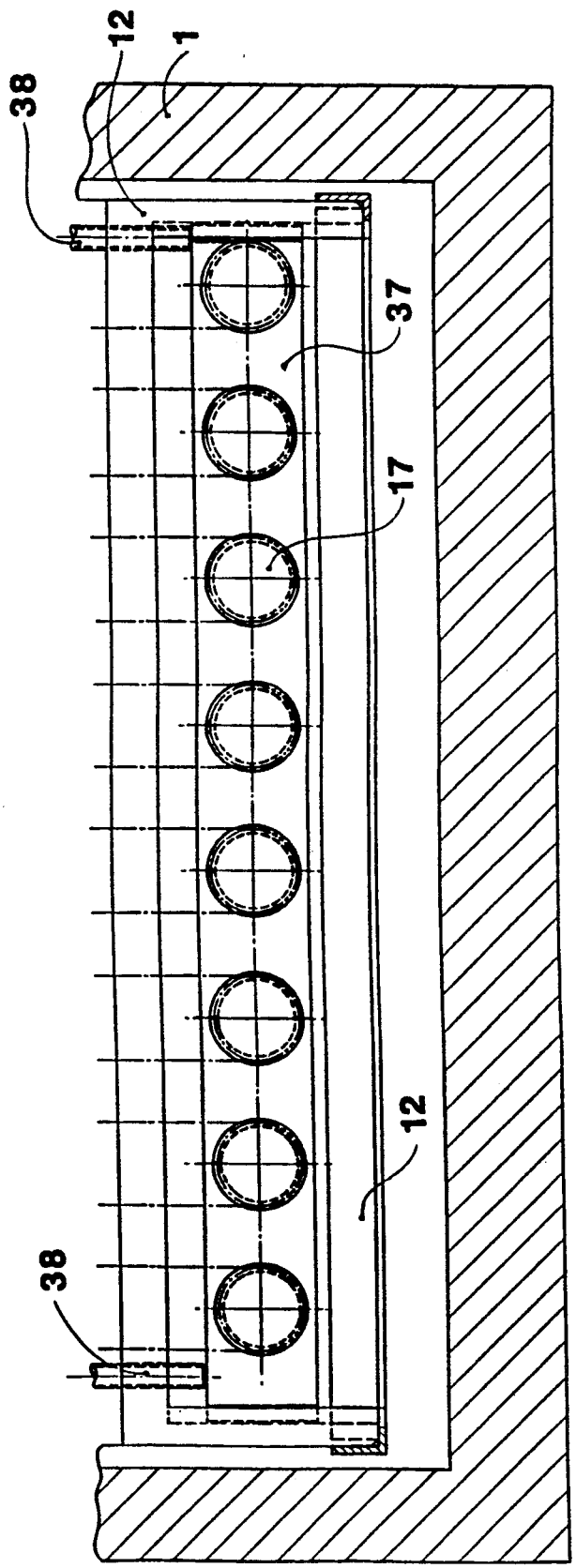
FIG. 9 is an elevational view of the chain tensioning mechanism of FIG. 8, taken from the bottom in that drawing figure and, as in FIG. 8, showing in cross-section a portion of a housing of the cryogenic storage apparatus.

As illustrated in FIGS. 2, 8 and 9, each endless conveyor chain 3 is partially wound over idler pulleys 17 and 17' rotatably mounted to inner frame structure 12 in two linear arrays at the top and the bottom of the housing. In addition, each conveyor chain 3 is partially wound about a further idler pulley 17" which serves to define horizontal chain portion 107.

Pulleys 17 of the lower rows re rotatably supported on opposite sides of an inner frame structure 12 by a bearing member 37 engineered to function as a chain tensioning device. Two long screws 38 on each side of frame structure 12 (FIGS. 3, 6, 8 and 9) push the bearing member down to tighten chains 3.

Frame structure 12 rests not on the bottom of housing 1 but is rather supported from the upper rim of the housing for facilitating adjustment of bevel gears 9 and 10 (FIG. 10). More particularly, frame 12 is secured to housing 1 via four alignment bolts 48 spaced around the perimeter of the upper rim of the housing. Aligning bolts 48 also aid in the alignment of cover 2 which is clamped to housing 1 by commercially available clamping levers 39 (see FIG. 10). Gaskets 40 and 40' are disposed between frame 12 and housing 1 and are made of graphite or other suitable insulating material.

As shown in FIG. 10, nitrogen container 18 is supported by brackets 41 from inner frame structure 12.

The process of depositing an ampule 16 into the cryogenic storage apparatus begins with the entry, into computer CC1 via keyboard 111, of a code number pre-assigned to the desired position of the ampule in the snaking array of support bars 4. Computer CC1 will compare the entered number with the numbers already in memory and verify the availability of the selected location. The code numbering system may simply take the form of a first set of consecutive numerals for successive bars 4 and a second set of consecutive numerals for adjacent ampule locations along a bar.

A tracking system is advantageously provided, exemplarily comprising computer CC1, together with an impulse module (not illustrated) on a driving shaft together with a decoder (not shown), both of which are commonly available. The decoder is operatively connected to computer CC1 for feeding thereto changes in the positions of endless conveyor chains 3, whereby the computer is at any time able to precisely locate the position of a given bar along path 103 within housing 1. Upon the selection of a particular ampule location (i.e., a specific bar 4 and a specific distance from one end of the bar), computer CC1 calculates the shortest direction of motion of chains 3 from the instantaneous position of the selected bar to access door 19 (FIG. 2) and will reverse the direction of chain drive, if necessary to minimize the search time.

Figure 11:
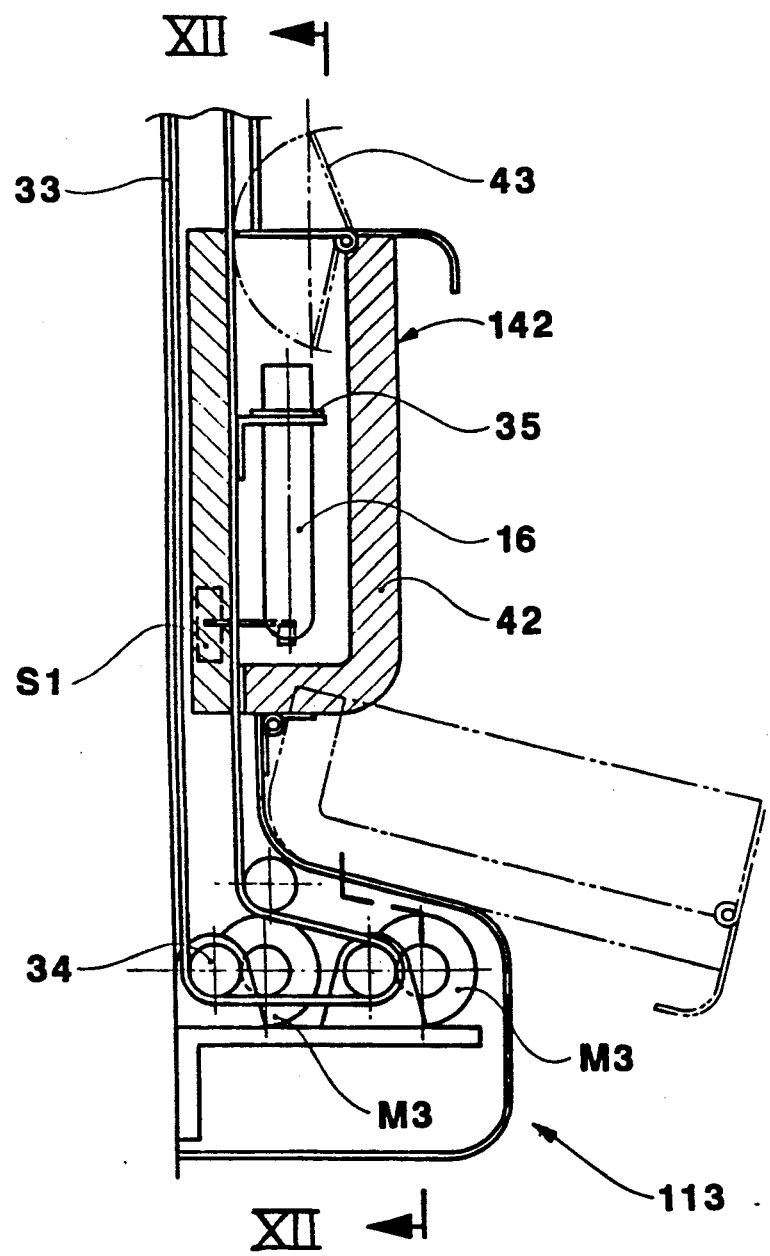
FIG. 11 is a partial cross-sectional view, on an enlarged scale, taken along line F—F in FIG. 1, depicting an intermediate storage container.
Figure 12:
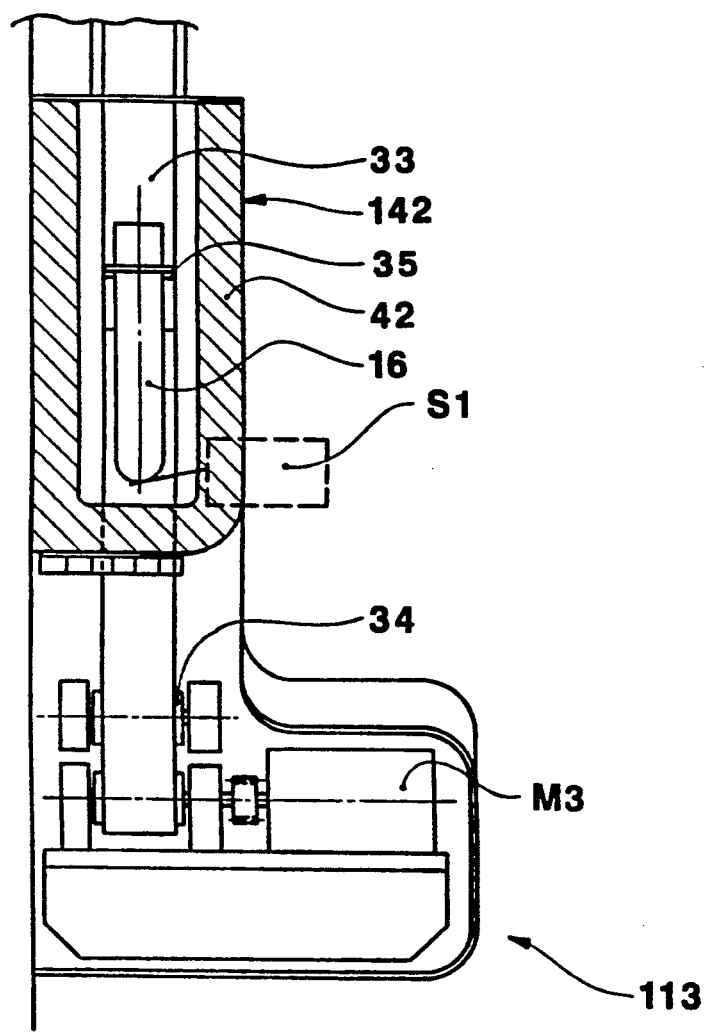
FIG. 12 is a partial cross-sectional view, on an enlarged scale, taken along line F—F in FIG. 11.

Further initial steps in the deposition of a specimen-containing ampule 16 in the cryogenic storage apparatus include the pivoting of an insulated cover member 42 of intermediate storage unit 142 from a closed position, illustrated in solid lines in FIG. 11, to an open position, shown in dot-dash lines. The ampule is then placed on a bracket member 35 attached to conveyor belt 33, cover member 42 being subsequently returned to the closed position. The ampule is now located temporarily inside a narrow insulated space of intermediate storage unit 142, enclosed by cover member 42 and by a spring loaded flap 43.

Upon placement of the ampule on bracket 35 (FIG. 11), a microswitch S1 signals computer CC1 that the ampule is ready to be deposited into the cryogenic storage apparatus. Computer activates lifting device 113 upon the arrival of the selected bar 4 precisely under door 19, which is closed at that stage of the ampule loading process. The activation of lifting device 113 consists in part of an energization of one of two motors M3 (see FIGS. 11 and 12) to drive conveyor belt 33 over pulleys 34 and thereby lift the ampule out from temporary storage inside intermediate storage unit 142 to a height determined by the location of a microswitch S7 (FIG. 3). Upon receiving a signal from microswitch S7, computer CC1 de-energizes the active motor M3, thereby halting the upward motion of the ampule.

While the ampule is being lifted from intermediate storage unit 142, ampule insertion and retrieval mechanism 50 is moved into a "zero" position, guided by dovetailed slide tracks 22 and 23 (FIG. 3) with a built-in gear track. Mechanism 50 is driven by a motor M1.

Motors M1, M2 and M4, switches S3, S4 and S6 and electromagnet 29 (FIG. 3) are supplied with power via a flat cable 49 (FIG. 1) extending from computer CC1 to ampule insertion and retrieval mechanism 50. Slide contacts 27 on a contact support 30 enable the transmission of electrical power to the motors, switches and electromagnet 29 of the ampule insertion and retrieval mechanism 50, even during rotation of an upper housing portion 25 thereof with respect to cover 2 of housing 1.

As illustrated in FIG. 3, electromagnet 29 is attached to a lower end of a spindle or rod 28 reciprocatingly driven by motor M4 via a belt 31 and grip rollers 44. Upon the reception of a signal from microswitch S7 and the subsequent arresting of conveyor belt 33, computer CC1 energizes motor M4 to shift rod 28 downwardly. Upon receiving a signal from microswitch S3, computer CC1 then deactivates motor M4, bringing the downward motion of rod 28 to a stop and energizes electromagnet 29 to form a magnetic link with a metal plate attached to the upper end of the ampule 16 held at the height of microswitch S7 by lifting device 113. The attachment of the metal plate on the ampule to the electromagnet closes a contact within the magnet, causing computer CC1 to again energize motor M4, this time in the reverse direction, to lift rod 28, together with the attached ampule. Upward motion of rod 28 is stopped by computer CC1 upon the reception thereby of a signal from microswitch S4.

As further depicted in FIG. 3, small magnets 32 are recessed into dovetailed side track or rail member 23 precisely at the location of the ampules on bars 4 within housing 1. Depending on the designated location at which the ampule carried by insertion and retrieval mechanism 50 is to be placed, microswitch S2 induces computer CC1 to stop motor M1 and to activate two motors M5 (each of which is a member of a pair, an active motor and a backup). The activated motors M5 are located at opposite ends of access door 19, which extends substantially across the width of cover 2.

Motors M5 rotate respective pinions 21 which in turn translate respective racks 20 secured to door 19, whereby door 19 slides along a sloped surface 119 (FIG. 3) of cover 2 and opens access to the interior of housing 1. Door 19 is pushed against sloped surface 119 by rollers 45 which apply a torque to racks 20 and, consequently, wedge-shaped door 119 under the action of a lever arm 46 and an adjustable weight 47. Door 19 is self-aligning and self-sealing due to its wedge-shaped cross section.

After microswitch S5 of the door opening and closing mechanism signals computer CC1 that door 19 has been opened, the computer stops motor M5 and also causes motor M2 of insertion and retrieval mechanism 50 to rotate upper housing portion 25 of the insertion and retrieval mechanism 180° around with the help of a ring gear which is part of dovetailed sliding carriage 21.

Two projecting pins 26 (FIGS. 3 and 5) connected to an inner surface of upper housing portion 25 of insertion and retrieval mechanism 50 cooperate with a microswitch S6 mounted to a sliding carriage member 24 of the insertion and retrieval mechanism to signal computer CC1 that rotation of 180° has been accomplished. The computer then deactivates motor M2 and simultaneously energizes motor M4 to lower rod 28, together with the ampule through the opened access door 19 and into the cooling chamber of the cryogenic storage apparatus.

Upon removal of an ampule from the cryogenic storage apparatus, a laser reader reads a bar code attached to the removed ampule to verify that the correct ampule has been retrieved. The bar code includes at least the name of the individual and an identification number, such as a social security number. The laser reader is capable of operating in a speed scanning or accelerated mode, which is particularly advantageous in the event that large number of ampules or speciments are being retrieved from the storage apparatus within a brief period of time.

The operation of the laser reader may be controlled by computer CC1. The computer may also be connected to a printer or other hard-copy output device so that, upon verification that the removed ampule is correct, a printed copy of various recorded statistics pertaining to the stored specimen ma be transported with the ampule.

In the absence of verification, the retrieved ampule is returned immediately to housing 1 and an alarm signal is generated for alerting an operator as to the error. In addition, or alternatively, an alphanumeric code identifying the retrieved ampule may be displayed on a monitor connected to computer CC1. If verification occurs, the removal of the ampule proceeds normally.

Microswitch S3 then induces computer CC1 to stop motor M4 and the downward motion of rod 28 and to de-activate electromagnet 29, thereby enabling the deposition of the ampule into an aperture in the selected bar 4 at the selected position therealong. Opened contacts within electromagnet 29 then cause computer CC1 to lift rod 28 out of the housing through door 19. A subsequent signal from microswitch S4 leads to the arresting of the upward motion of the rod and causes computer CC1 to activate motors M5 to close door 19 and motor M6 to recommence continuous motion of bars 4 and their ampules 16 along path 103 through housing 1.

Figure 4:
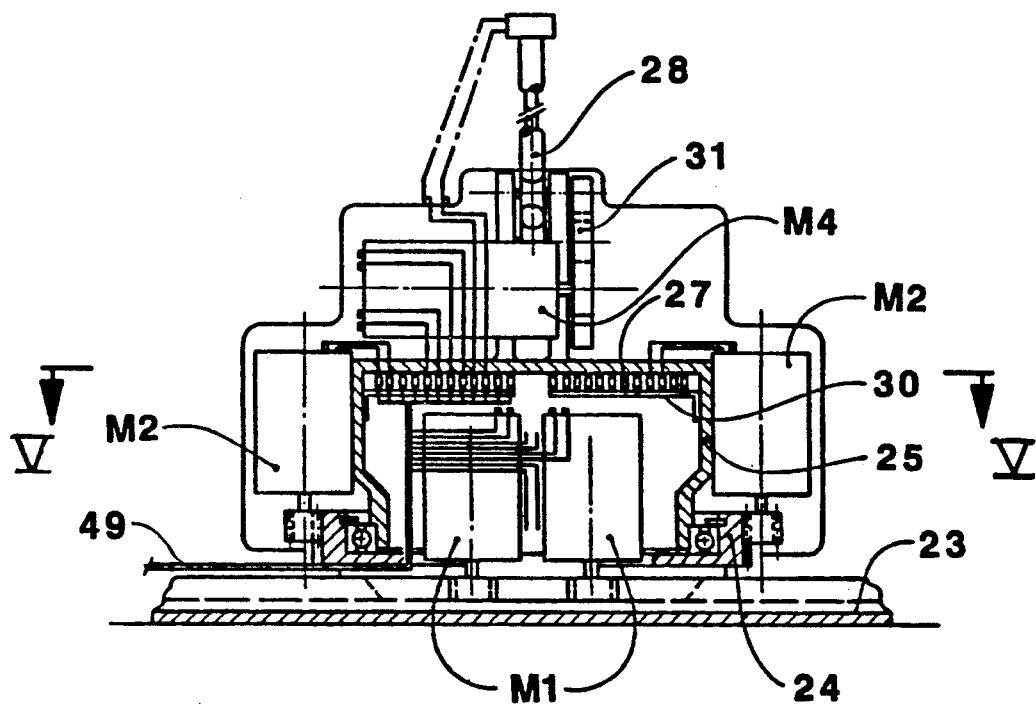
FIG. 4 is a partial cross-sectional view taken along line B—B in FIG. 3, showing a lifting mechanism.

As shown in detail in FIGS. 3 and 4, insertion and retrieval mechanism 50 includes dovetailed rail member 24 which is operatively fastened to cover 2 of housing 1 and extends parallel to door 19. Carriage 24 is slidably mounted to rail member 24 for motion therealong. Motor M1 (or its normally inactive backup) serves to move the carriage 24 along rail member 24 via a rack and pinion transmission assembly. Under the control of computer CC1, electromagnet 29 is raised and lowered by rod 28 to secure a hold on a selected ampule 16 positioned in housing 1 in juxtaposition to door 19. Motors M4 serve to move rod 28 and electromagnet 29 a linear path through door 19. Upper housing portion 25 is rotatably mounted to carriage member 24, while motors M4 are mounted to housing portion 25. Rotary drive motors M2 (FIG. 4) are operatively connected to the rotatable housing portion for rotating the same relative to carriage member 24.

Figure 13:
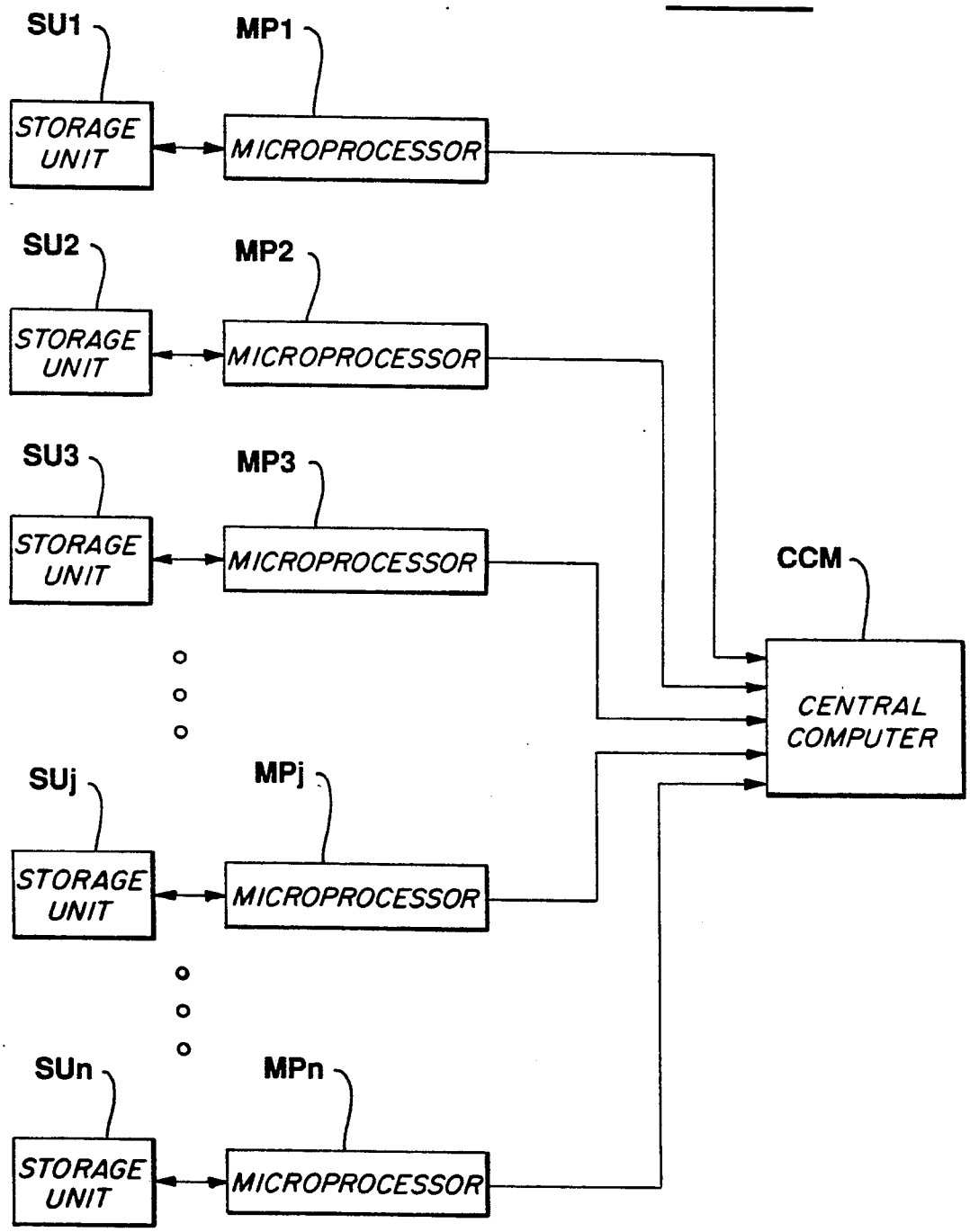
FIG. 13 is a block diagram of a system including a multiplicity of storage apparatuses such as illustrated in FIGS. 1-12.

As depicted in FIG. 13, a storage system comprises a multiplicity of individual storage units SU1, SU2, SU3 . . . SUj . . . SUn possibly disposed at widely spaced locations. Each such storage unit is connected to a respective control microprocessor or computer MP1, MP2, MP3 . . . MPj . . . MPn disposed at the same location as the storage unit. Each storage unit SU1-SUn and its associated local microprocessor MP1-MPn may be essentially identical to the cryogenic storage apparatus described hereinabove with reference to FIGS. 1–12. Microprocessors MP1–MPn are connected via respective bidirectional lines to a remotely located central computer CCM.

Central computer CCM performs a monitoring and alert function. It is contemplated that specimens are subject to duplicate storage, each specimen having at least one essentially identical counterpart stored in a different one of the storage units UN1-UNn. Upon the receipt of a request for the specimen, each storage unit SU1-SUn containing one of the duplicate sample retrieves the respective sample under the control of its respective microprocessor MP1-MPn. As the samples are removed from the cryogenic storage chambers of units SU1-SUn, the bar code verification devices of those storage units cooperate with the respective microprocessors MP1-MPn to verify that the retrieved ampule corresponds to the requested specimen. The results of that verification step, including the identities of the retrieve samples, are communicated to central processor CCM. The central processor then checks that the retrieved samples are in fact duplicate samples. In the event that the check yields a difference between the retrieved samples, a signal is transmitted to the respective microprocessors MP1-MPn for alerting operating and maintenance personnel as to a possible malfunction. Once the cross-check is verified by central computer CCM, the computer may then instruct microprocessors MP1-MPn as to which of the retrieved samples are to be transported in response to the specimen request.

In the event that a malfunction occurs in a cryogenic storage unit 202 (FIGS. 14 and 15) such as described hereinabove with reference to FIGS. 1-12, specimen-containing ampules 16 stored in the malfunctioning unit are quickly and automatically transferred therefrom to another cryogenic storage unit 204 which is structurally similar to the first unit. The automatic transfer of the ampules is effectuated via a transfer apparatus 206.

Figure 14:
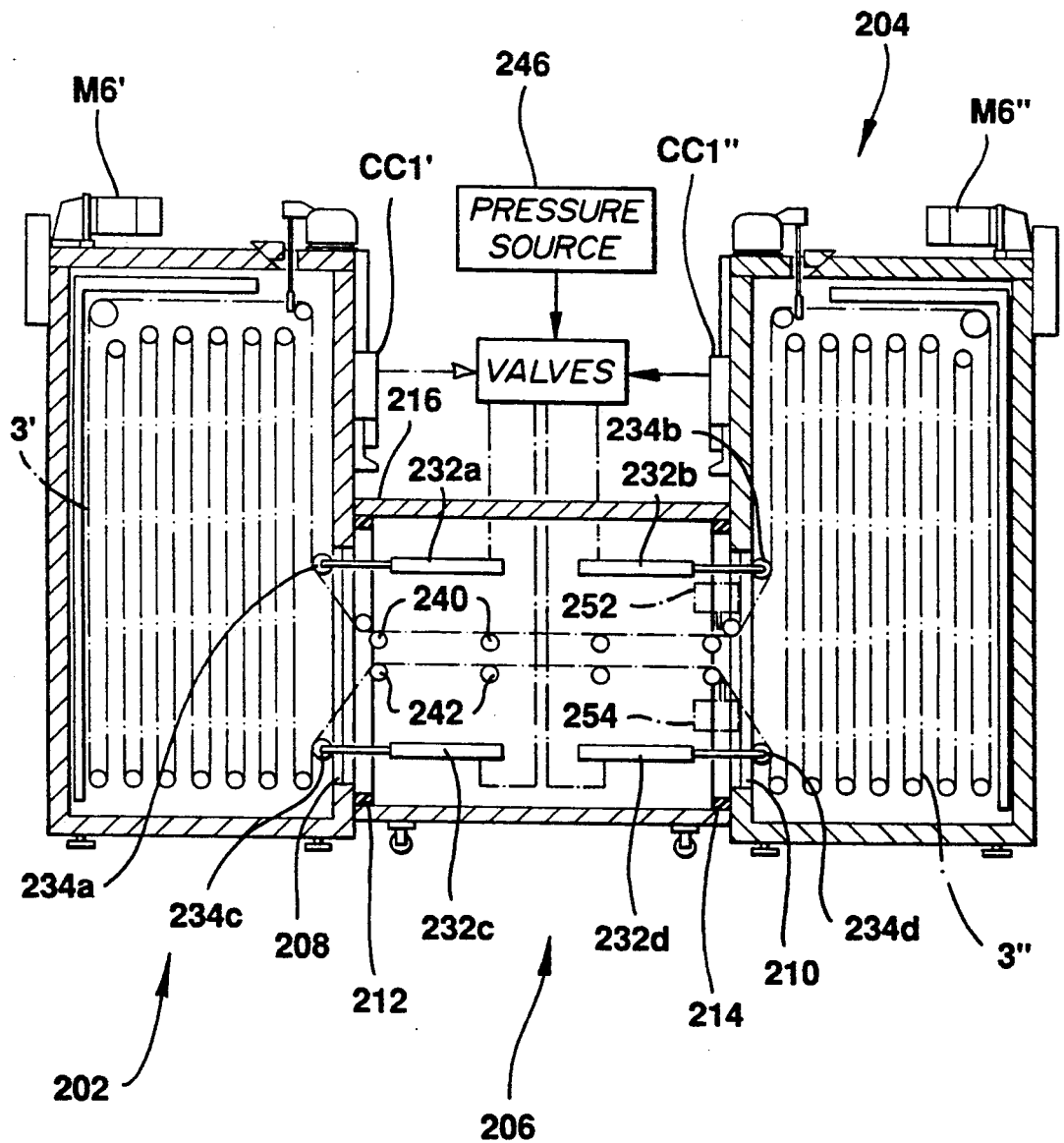
FIG. 14 is a schematic cross-sectional view, similar to FIG. 2, of two cryogenic storage apparatuses in accordance with the present invention, showing a device for transferring specimen-containing ampules from one of the storage apparatuses to the other.

As shown in FIG. 14, transfer apparatus 206 is connected on opposite sides to storage units 202 and 204. Each storage unit 202 and 204 is provided on a front side with a slidably removable or shiftable door 208 and 210 and a resilient rib 212 and 214 perimetrally surrounding the respective door opening. Transfer apparatus 206 includes a four sided housing 216 which engages ribs 212 and 214 in an essentially fluid-tight fit.

Figure 15:
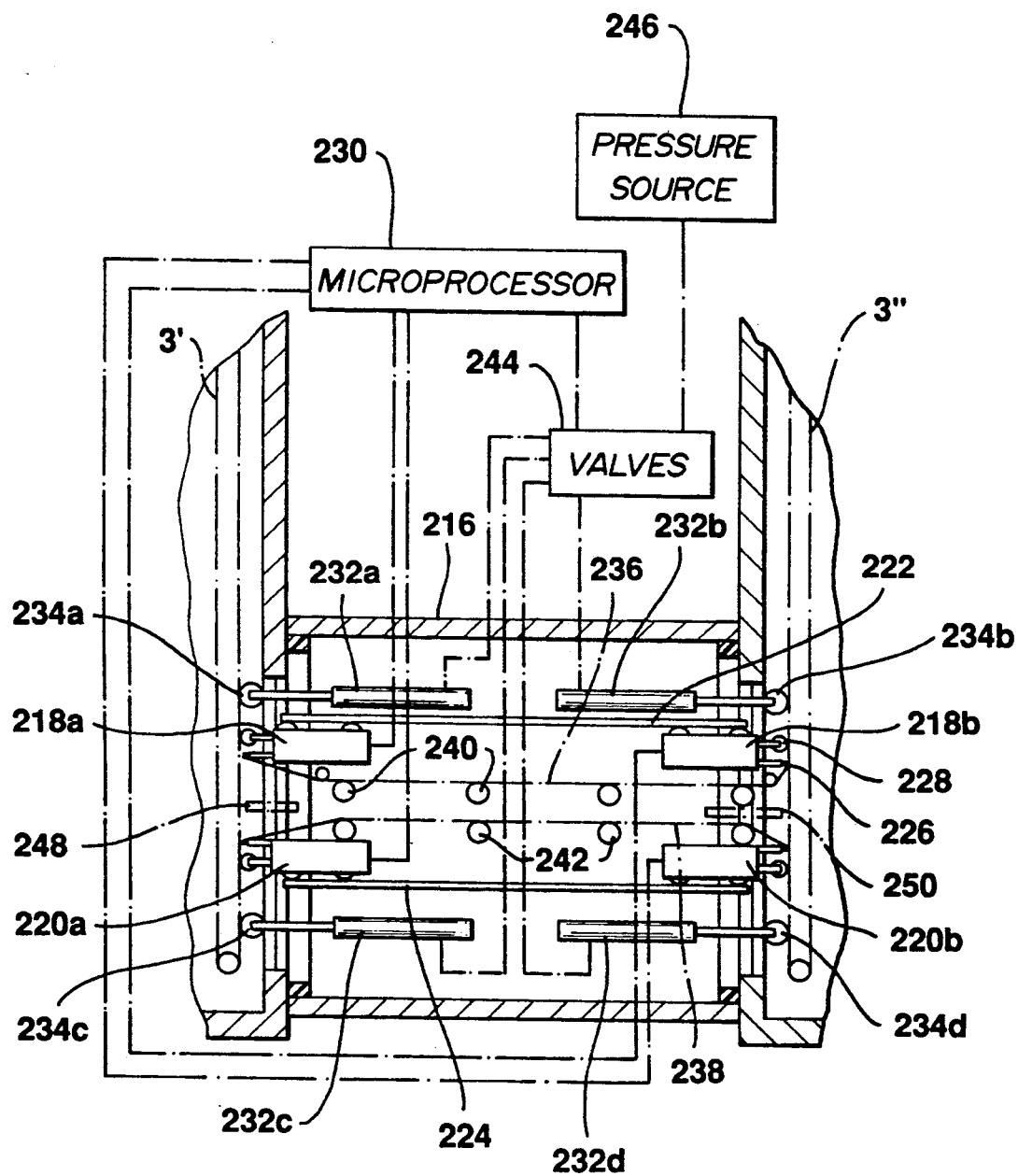
FIG. 15 is a schematic cross-sectional view, on an enlarged scale, of the device of FIG. 14 for transferring specimen-containing ampules from one cryogenic storage apparatus to another.

As illustrated in FIG. 15, transfer apparatus 206 comprises four pairs of cars 218a, 218b and 220a, 220b (only two pairs visible in the drawing) movably mounted to rails 222 and 224. Each car 218a, 218b, 220a, 220b includes a jaw mechanism 226 and a roller 228. The operations of cars 218a, 218b, 220a, 220b, including their motions along tracks or rails 222 and 224, as well as the opening and closing of jaw mechanisms 226, are controlled by a microprocessor 230, which may be either of the computers CC1' or CC1" of storage units 202 and 204. Transfer apparatus 206 further includes eight pneumatic or hydraulic cylinders 232a, 232b, 232c, 232d (only four shown in the drawing) each carrying a respective roller 234a, 234b, 234c, 234d at the free end of its plunger. In addition, at the onset of a transfer operation, on each of two opposite sides of housing 216, two chain segments 236 and 238 extend over respective pluralities of rollers 240 and 242. Each chain segment 236 and 238 is gripped at its opposite ends by the jaw mechanisms 226 of respective cars 218a, 218b and 220a, 220b.

Upon the disposition of transfer apparatus 206 between storage units 202 and 204, microprocessor 230 actuates valves 244 (connected to pressure source 246) to cause cylinders 232a, 232b, 232c, 232d to extend their plungers so that rollers 234a, 234b, 234c, 234d are in contact with chains 3' and 3" of storage units 202 and 204. In addition, cars 218b and 220b are moved along rails 222 and 224 so that jaw mechanisms 226 are able to attach the free ends of chain segments 236 and 238 to chain 3". Upon that attachment, microprocessor 230 shifts cars 218a, 218b, 220a and 220b towards storage unit 202 to enable the attachment of the other ends of chain segments 236 and 238 to chain 3'. Upon the securing of both ends of chain segments 236 and 238 to chains 3' and 3", chains 3' and 3" are severed by cutting devices 248 and 250 at points between the ends of chain segments 236 and 238. Microprocessor 230 then energizes one or both motors M6' and M6" of storage units 202 and 204 to move ampule-holding chains 3' and 3" between storage units 202 and 204, thereby transferring all the ampules stored in one unit 202 to the other unit 204.

Upon completion of the transfer, a pair of combination joining and severing devices 252 and 254 (FIG. 14) are activated by microprocessor 230 to reattach chain 3', now in storage unit 204. Door 210 is then closed and transfer apparatus 206 separated from storage units 202 and 204.

It is to be noted that devices 252 and 254 may be incorporated into cars 218a, 218b, 220a and 220b. In addition, computers CC1' and CC1" may be programmed to track the location of a predetermined severing point along chains 3' and 3". That severing point may be provided with a clasp or latch (not illustrated) which is unlocked rather than cut at the onset of a transfer operation. Similarly, the reattachment of chain 3' by devices 252 and 254 may be effectuated by application of a clasp to different portions of the chain juxtaposed by the joining and severing devices 252 and 254.

It is to be noted that other ampule transfer devices may be constructed in accordance with the principles of the invention. For example, the ampules may be removed from the upper end of a malfunctioning storage apparatus, rather than from the lower end as shown in FIGS. 14 and 15, by a transfer apparatus essentially identical in structure and function to that shown in those drawing figures. In such a case, the transfer apparatus would operate where the storage medium is a liquid such as liquid nitrogen, as well as where the storage medium is low-temperature nitrogen vapor or another gas.

Figure 16:
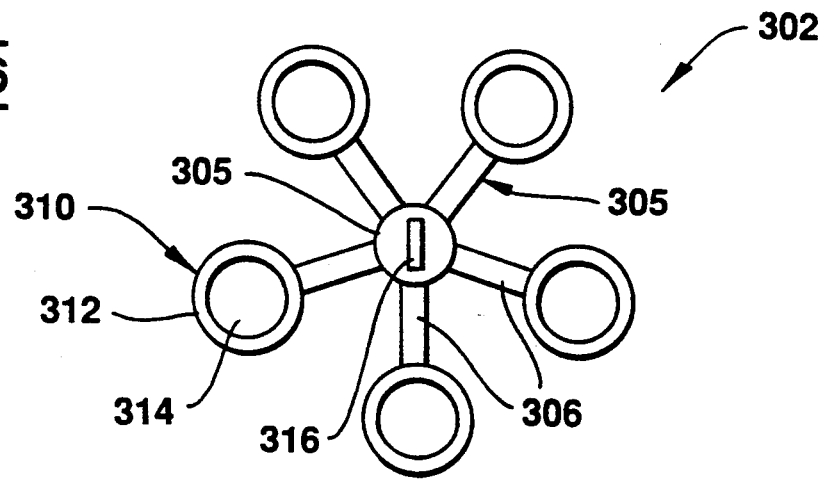
FIG. 16 is a top view of an ampule cluster according to a specific feature of the present invention.
Figure 17:
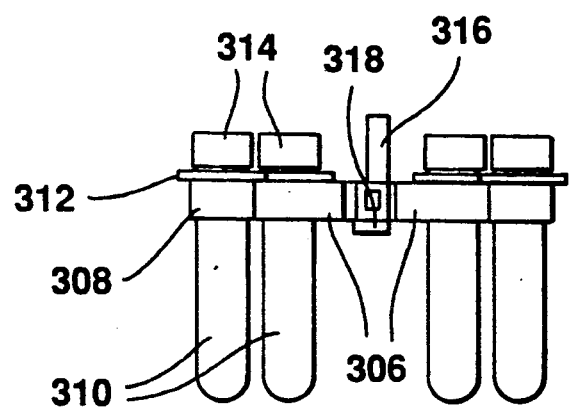
FIG. 17 is a side elevational view of the ampule cluster of FIG. 16.

As depicted in FIGS. 16 and 17, a cluster ampule assembly 302 includes a star-shaped holder 304 with a central node element 305 and five radiating arms or spokes 306 each provided at an outer end with a ring 308. Seatable in each ring 308 is a respective ampule 310 having an annular flange 312 at an upper end and a magnetic cap 314. Node element 305 is provided with a carrier ring 316 for enabling removal of the entire ampule cluster through a doorway in a cryogenic storage unit such as that illustrated in FIGS. 1 and 2. In addition, holder 304 is provided on the underside of node element 305 with a lug 318 for insertion into a hole or recess (not illustrated) in a support bar 4 (see FIG. 5).

Figure 18:
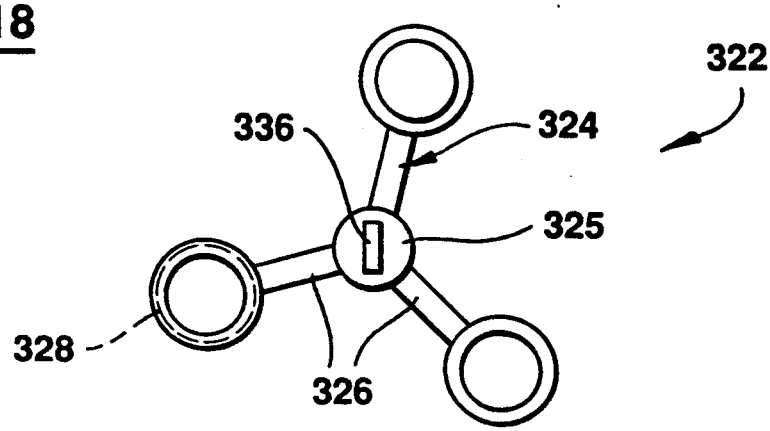
FIG. 18 is a top view of another ampule cluster according the invention.

FIG. 18 shows another cluster ampule assembly 322 includes a holder 324 with a central node element 325 and a three radiating arms or spokes 326 each provided at an outer end with a ring 328. Node element 325 has a carrier ring 336 on an upper side for enabling insertion and removal of the entire ampule cluster through a doorway in a cryogenic storage unit.

In use, five samples of the same specimen are placed in the five ampules 310, which are then stored in the cluster assembly 302 in a cryogenic storage apparatus pursuant to the invention. If two samples are requested, two ampules 310 are removed and the other three are transferred to a three-ring holder 324 and then returned to the cryogenic storage apparatus. Of course, four-ring and two-ring holders may also be provided.

Although a storage apparatus, facility or system in accordance with the invention may be used to store virtually any item which is not of a prohibitively large size, such an apparatus, facility or system is particularly well suited to storing umbilical cords and/or umbilical cord segments for uses described in commonly owned copending U.S. patent application Ser. No. 455,170 filed Dec. 22, 1989, the disclosure of which is hereby incorporated by reference.

As discussed in U.S. patent application Ser. No. 455,170, umbilical cords from infants born within a prescribed territory (a city, county, state or an entire country) are sectioned, preserved and stored. Also stored is information pertaining to each individual such as the infant's name, birth statistics and any pertinent information as to genetic predisposition to certain diseases. Pursuant to the instant invention, this information is stored in computer CC1 or local microprocessors MP1, MP2 . . . MPj . . . MPn and can be additionally transmitted to central computer CCM.

As further discussed in U.S. patent application Ser. No. 455,170, the preserved umbilical cords or portions thereof are subsequently made available for medical identification, research purposes or therapeutic treatment upon proper request.

Specifically, upon the birth of an infant, its umbilical cord is severed into one or more segments. The severing may be accomplished by any known technique. See, for example, U.S. Pat. No. 4,648,401 to Philip D. Mattson, the disclosure which is incorporated by reference herein. A preferred apparatus and technique is disclosed in commonly owned U.S. patent application Ser. No. 471,084 filed Jan. 26, 1990, the disclosure of which is hereby incorporated by reference herein.

Upon or prior to the severing of an umbilical cord segment, the ends of the segment are closed to retain all biological materials contained within the umbilical cord. The closure may be accomplished by tying or with synthetic resin end caps or other clamps or staples (see U.S. Ser. No. 471,084), or otherwise sealed. The closure procedure is implemented on a free end of the umbilical cord segment while that end is clamped by a hemostat or other instrument. In an alternative procedure, the ends of an umbilical cord are dipped into a cryogenic bath to close the ends by freezing.

As discussed in both U.S. patent application Ser. No. 455,170 and U.S. patent application Ser. No. 471,084, the umbilical cord segments may be washed, preferably prior to sectioning of the cord to minimize the loss of umbilical cord blood. Alternatively, each segment may be washed subsequently to the sealing of the ends.

Upon the sectioning of an umbilical cord and the closing of the segment ends, each segment is then preserved preferably by immersion in a cryogenic coolant such as liquified nitrogen. Alternatively, a sealed umbilical cord section is first placed in a suitable thin walled container such as a polyethylene bag or vial, as disclosed in U.S. patent application Ser. No. 471,084. The container is then immersed in a low-temperature fluid. Such a fluid may take the form of liquid nitrogen, liquid carbon dioxide or a chlorofluorocarbon mixture such as those described in U.S. Pat. No. 4,803,842 to Coehlo, the disclosure of which is incorporated by reference herein.

The umbilical cord segments may also be preserved by other techniques, such as freeze drying. Freeze-drying is generally not preferred because of the effects of the freeze-drying process on structures of various biological components such as cell membranes. However, inasmuch as certain biochemical components such as DNA, RNA and various proteins may be stored intact by a freeze-drying technique, preservation of at least on segment of each umbilical cord by freeze-drying may be useful.

A particular technique for preserving liposomes is disclosed in published PCT Application No. PCT/US85/01502, Publication No. WO 86/01103. Liposome preparations are dehydrated under reduced pressure in the presence of one or more sugars, preferably the disaccharides trehalose and sucrose. The amounts of the sugars used depends on the type of sugar and on the characteristics of the liposomes to be protected. Freezing of the liposomes prior to dehydration is optional.

In an additional series of steps, various constituents, for example, blood and endothelial vein cells, of an umbilical cord are isolated from an umbilical cord sample at the birth of an infant. The blood may be aspirated from an umbilical cord or segment by an apparatus and technique disclosed in U.S. patent application Ser. No. 471,084. The constituents are analyzed and typed according to known methods. For example, the blood type, the blood protein concentrations, the karyotype, the HLA and other factors are all determined and recorded. These umbilical cord parameters are included in the general statistical information pertaining to the personal history of the individual including his or her name, parentage, birth date, weight, sex, etc., which is generally collected by a health care institution such as a hospital. Further personal history information preferably includes genetic history information pertaining, for example, to the predisposition of the individual to certain diseases.

Upon the umbilityping of the contents of the umbilical cord of a new-born infant, as described hereinabove, the umbilification information is transmitted, together with the personal history statistics, to an information storage facility, such as central computer CCM and/or any of the local microprocessors or computers MP1-MPn. The information is preferably encode in digital form and is transmitted via a communications link (telephone, wireless, satellite) to the storage facility.

Each microprocessor or computer MP1-MPn is a information repository containing all the umbilification and personal history information for all individuals born after a certain date in the prescribed area (a hospital, a city, a county, several counties, a state, several states or an entire country). The stored information includes, for each parcel of umbilification and personal history information, the location of the individual's umbilical cord segment or segments.

Umbilification and personal history (including genetic history) information for all individuals born in a larger geographical area, such as several countries or even the entire world may be stored in central computer CCM. That computer, as well as the local microprocessors or computers MP1-MPn, are provided with programming for implementing the organization of the umbilification and personal/genetic information into categories or types each relevant to a particular use of the stored umbilical cord materials. One such categorization, for example, would be into bone marrow and/or stem cell types. The categorization would be based not only by blood type but also on ethnic background since it has been determined that bone marrow from a donor of the same ethnic background as the recipient has a better chance of successful implantation, without rejection, than marrow from a donor of a different ethnic background than the recipient. The categorization would be further refined by other information, including genetic composition, obtained from analysis of the umbilical cord materials.

Upon freezing of an umbilical cord segment, the segment is conveyed to a cryogenic storage unit SU1-SUn which contains umbilical cord segments for all individuals born after the prescribed date in the prescribed locale.

It is contemplated that several umbilical cord segments for each newborn individual are prepared and transferred to a cryogenic storage unit SU1-SUn for future utilization under different circumstances. As a precaution, it is recommended that one or more segments for each individual are sent to a second, back-up facility essentially duplicating the umbilical cord and information contents of the first cryogenic/information storage facility.

Umbilical cord segments are maintained in a cryopreserved or freeze-dried state at a cryogenic storage facility for an indefinite period. The facility receives requests for items stored at the facility. Upon receiving a request for a deposited stored umbilical cord segment, that segment is retrieved from storage and conveyed at least in part to another location.

It is within the contemplation of the invention that the umbilical cord segments may remain viable for a limited period of time depending on the particular preservation and storage techniques being used. In that event, local computers MP1-MPn and central computer CCM are provided with the preservation and/or birth dates of the umbilical cords. The computers then keep continuous track of the storage periods (age data) for all the stored segments and periodically, for example, daily or weekly, via a printer or other peripheral output device, provide to operating personnel information regarding which umbilical segments are approaching the end of their viability period. The operators may then make a decision to retrieve any deteriorating umbilical cord specimens and, for example, send them to scientists and doctors for research purposes.

The information may be communicated to the operating personnel, e.g., via a printer or monitor, automatically and on a periodic basis, as discussed above, or in response to requests from the operators. In either event, the information may include any of the stored information, including the family lineage. This information may be provided by the central computer CCM to operating personnel at the associated central facility, as well.

Computers MP1-MPn are programmed to track the stored umbilical cord segments by type, for example, by blood type, DNA composition and lineage or geneology. Thus, in the event that a request is received for umbilical cord blood of a particular type, the computer can quickly locate and retrieve the umbilical cord specimens having blood of the requested type.

Moreover, computers MP1-MPn are able to physically move the specimens relative to one another, i.e., to change their storage locations in the respective storage units SU1-SUn, whereby all specimens of the same type (e.g., same blood type, genetic composition or lineage) are stored in the same neighborhood within the storage chamber of the storage unit. To that end, as schematically illustrated in FIG. 19, a storage apparatus 402 with a housing 404 defining a storage chamber 406 and a conveyor assembly 408 for moving along a predetermined path 409 ampules 410 containing umbilical cord specimens (not separately illustrated) includes a transfer mechanism 412 inside chamber 406 for transferring ampules from the conveyor assembly to a fixed temporary storage rack 414 and back to the conveyor assembly after the conveyor has moved a predetermined distance under the control of a microprocessor or computer CC2.

Figure 19:
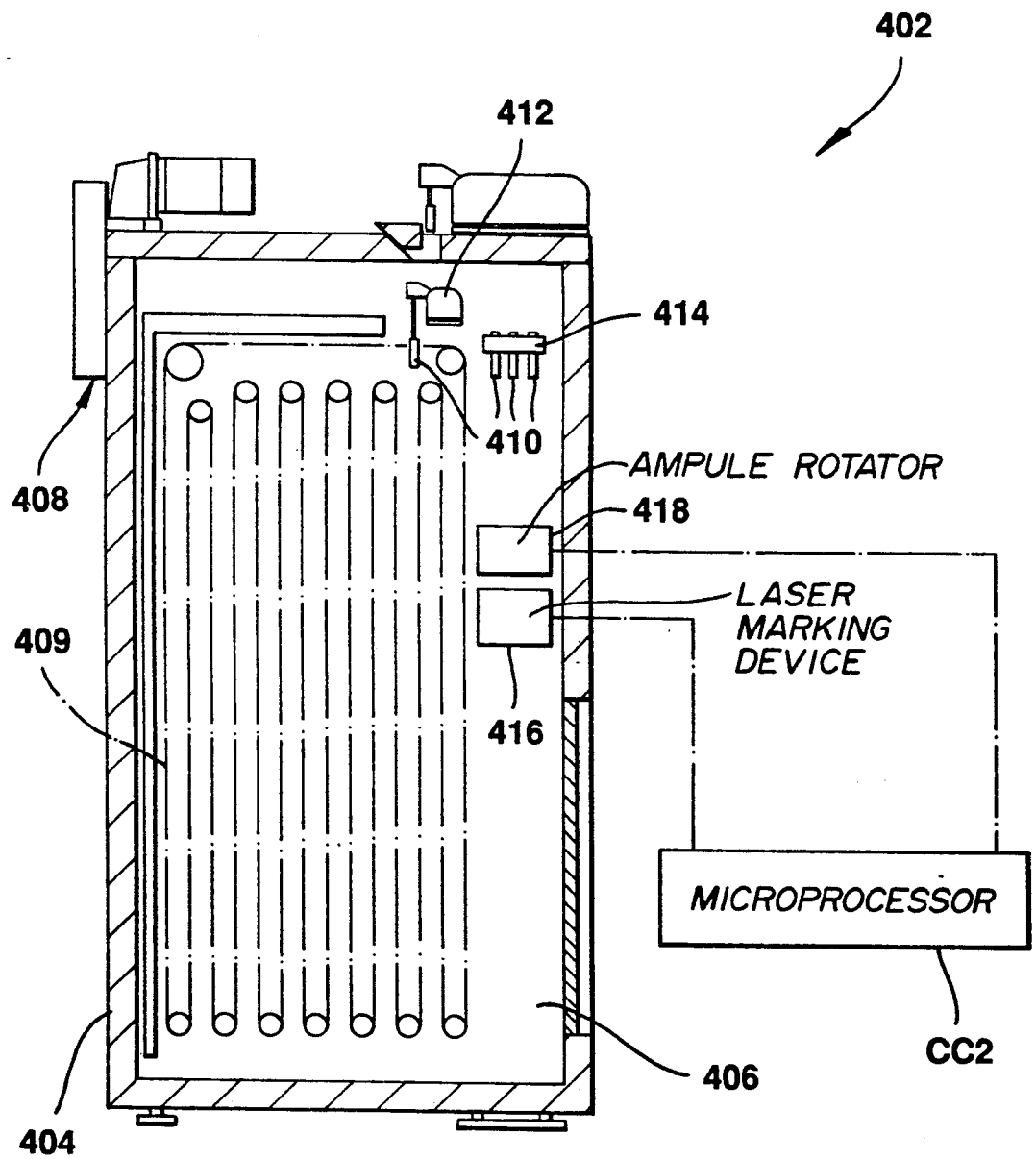

As illustrated in FIG. 19, a storage apparatus 402 in accordance with the invention may be provided inside housing 404 with a laser or other marking device 416 connected to microprocessor or computer CC2 for adding information, in response to signals from the microprocessor or computer, to the bar codes on selected ampules. Computer CC2 is connected to conveyor assembly 408, as described hereinabove with respect to computer CC1 and FIGS. 1-12. Computer CC2 can arrest the operation of conveyor assembly 408 in order to stop a selected ampule in the region of laser marking device 416. An ampule rotator 418 is also provided in housing 404 for engaging the selected ampules and turning them about a vertical axis so that laser marking device 416 can apply annular marks of precalculated widths to the selected ampules. Laser marking device 416 and ampule rotator 418 may be shiftably mounted to rails or tracks (not illustrated) in the same manner as insertion and retrieval mechanism 50 (FIG. 3) is mounted to rail 23 so that the marking device and the rotator may be moved parallel to the support bars (4 in FIGS. 1 and 3).

Umbilical cords and/or umbilical cord segments and/or other organs such as kidneys, spleens or livers or portions thereof may be stored in apparatus 402 independently, that is, without vials or ampules 410. In that event, the various umbilical cords or organs may be suspended by hooks or clamps from the support bars (4 in FIGS. 1 and 3). In addition, laser marking device 416 may apply a bar code or other information encoding marks directly to the outer surface of the organ. In the case that marking device 416 comprises a laser, the marking is accomplished through a burning technique. Alternatively, the marking device may take the form of an injection mechanism for depositing a biologically inert dye or ink immediately below the outer surface of the organ (as in the tattooing arts).

As illustrated in FIG. 19, housing 404 may be provided with another access door for enabling the simultaneous removal of several specimens from the storage chamber 406.

In the event that the cluster ampule assemblies of FIGS. 16-18 are used, the doorway accessing storage chamber 406 is, of course, large enough to enable the insertion and removal of the largest ampule cluster assembly (whether five or more ampules). In addition, the distance between the vertically oriented folds of path 409 is large enough to accommodate the increased width of the ampule clusters.

As further discussed in U.S. patent application Ser. No. 455,170, several uses of consitutent parts of umbilical cords are already known. It is known, for example, that umbilical cord blood includes hematopoietic stem and multipotential (CFU-GEMM), crythroid (BFU-E), and granulocyte-macrophage (CFU-GM) progenitor cells utilizable in hematopoietic reconstitution as an alternative to bone marrow transplantation. See, e.g., "Human umbilical cord blood as a Potential Source of Transplantable Hematopoietic Stem/Progenitor Cells" by Hal E. Broxmeyer et al., *Proceedings*, National Academy of Sciences, Vol. 86, pp. 3828-32 (1989), which is incorporated by reference herein, and references cited in the article. Broxmeyer et al. noted that umbilical cord blood contains numbers of CFU-GM cells well within the range of bone marrow CFU-GM cells that have been associated with successful autologous and major histocompatibility complex-matched allogenic bone marrow transplantation. The conclusion to be drawn from that study is that cells from human umbilical cord blood from a single individual are sufficient for autologous reconstitution and for major histocompatibility complex-matched allogenic hematopoietic reconstitution.

In a recent clinical study described in the article, incorporated by reference herein, "Hematopoietic Reconstitution in a Patient With Fanconi's Anemia by Means of umbilical cord blood From an HLA-Identical Sibling," by Elaine Gluckman et al., *New England Journal of Medicine*, Vol. 321, No. 17, pp. 1174-78 (Oct. 26, 1989), a five year-old boy having classic symptoms and malformations of Fanconi's anemia received cryopreserved umbilical cord blood, isolated from the umbilical cord prior to freezing, from a sister shown to be unaffected by the disorder, to have a normal karyotype, and to be HLA-identical to the patient. After a pretreatment including the oral administration nonabsorbable antibiotics and of cyclophosphamide for pretransplantation conditioning and further including the application of irradiation to the thoracoabdominal region by a linear accelerator, cryopreserved umbilical cord blood was thawed and infused into the patient without further processing. The blood had been obtained from the sister's umbilical cord and the placenta and transported at ambient temperature by overnight courier to a laboratory for analysis, cryopreservation and storage. The blood was frozen in dimethyl sulfide at a final concentration of 10 percent. Upon thawing of the umbilical cord blood, it was found that eighty-two percent of the nucleated cells were viable. As suggested by the Gluckman et al. article, other conditions for which bone marrow transplant is indicated may be treated with the use of cord blood.

Accordingly, blood from cyropreserved umbilical cord segments may be used, in accordance with the invention, in bone marrow reconstitution. Upon a blood typing of the patient, in which specific values of umbilityping parameters are determined for that individual, the determined umbilification information is transmitted to the information repository, where it is compared with the digitally stored blood type and other information pertinent to stored umbilical cord segments. Upon detecting a match, the corresponding umbilical cord segment is transferred in cryopreserved state to the requesting health care institution.

In a method for therapeutically treating a patient, at least a portion of a preserved umbilical cord segment is received from a storage facility upon following the procedure set forth above. A biological sample or component is then isolated from the umbilical cord segment and is used to treat the patient. The umbilical cord segment is warmed prior to the isolation or extraction of the desired molecule, cell, tissue or organ portion.

If the isolated or extracted component takes the form, for example, of a stem cell from the umbilical cord blood, the cell is the infused into the body of the patient with other stem cells and possibly progenitor cells from the same umbilical cord segment and from other umbilical cord segments whose specific unbilification parameters match the umbilification parameters determined for the patient. Such an allogenic hematopoietic reconstitution can be implemented after the preservation, umbilityping and storage of several millions of umbilical cord segments.

In an alternative procedure for an allogenic hematopoietic reconstitution, the stem cells from one matched umbilical cord segment are replicated in vitro and subsequently injected into the patient. A method for replicating bone marrow samples is described in U.S. Pat. No. 4,721,096 to Naughton et al., pertinent portions of which are hereby incorporated by reference herein. In that patent, the bone marrow sample is obtained from a bone or bones of a donor. Pursuant to the invention, bone marrow cells (stem cells, progenitor cells) are obtained from one or more preserved umbilical cord segments.

It is also within the contemplation of the instant invention that an autologous hematopoietic reconstitution can be effectuated upon in vitro replication of stem cells obtained from a preserved specimen of the patient's own umbilical cord. Of course, in any hematopoietic reconstitution technique involving replication of the required cells, only a small segment of a single umbilical cord is needed.

It is to be noted that a program of storing umbilical cord segments for all individuals born after a prescribed date within a predetermined geographical area provides a bank or repository of human molecular, cellular, tissue and organic components for research and therapeutic purposes. This repository shall become increasingly valuable as more techniques are developed for isolation and use of various umbilical cord components. In addition, a store of biological and personal history information is provided for us with the preserved umbilical cord segments.

Umbilification technology in accordance with the present invention shall provide a repository of raw material for research into diseases affecting entire groups of people, for example, sickle-cell anemia or Tay-Sachs disease. This technology will also enable the tracing of changes in genetic compositions of families giving rise to a predisposition to such afflications as cancer. In addition, changes in genetic make-up due, for example, to radioactive fall-out from a nuclear catastrophe or accident can be traced from umbilical cord segments and associated information for all the people born in the area of the accident.

It is to be noted that the bank or repository of human molecular, cellular, tissue and organic components for research and therapeutic purposes is built from material (umbilical cord segments) which could otherwise be discarded after the infants' births. The bank or repository is thus implemented without any invasive surgery or other invasive extraction techniques.

A method in which umbilical cord sections are cryopreserved in accordance with the present invention would have utility even if the various cells in the umbilical cord, including blood cells and endothelial vein cells, were not found in a particular instance to be viable in sufficient numbers. It is known that DNA may be cryopreserved for a significant period. As mentioned above, Vivigen, Inc., a company in Santa Fe, New Mexico, has announced its readiness to cryogenically store DNA and RNA for medical and research purposes. Pursuant to the present invention, the DNA and/or RNA in a cryopreserved umbilical cord section may be used to identify or confirm the identity of an individual who is, for example, unconscious from an accident or a disease or who refuses to provide proof of his identity. The comparative analysis of the individual's genetic material with the genetic material of an umbilical cord section, performed by known techniques, such as those disclosed in U.S. Pat. Nos. 4,772,549 and 4,861,708 to Philippe M. Frossard, the disclosures of which are incorporated by reference herein, may be supplemented by blood typing and other histological, cellular and molecular assay techniques.

Accordingly, in a method for identifying a person, a preserved umbilical cord segment is received from a storage facility, while information recorded at the birth of an infant attached to an umbilical cord from which said umbilical cord segment was severed and subsequently preserved is also received. The recorded information includes statistics pertaining to the newborn and his or her birth, together with an identification of the preserved umbilical cord segment. In a further step, biological material of a type to be found in umbilical cords (genetic material, blood including stem cells, etc.) is isolated and extracted from an individual to be identified and analyzed to determine a plurality of predetermined umbilification parameters. The determined values of the predetermined parameters are then compared with the received information to determine whether the individual to be identified is the same person a the infant from which the preserved umbilical cord was obtained. As described hereinabove, the parameters used for the identification process may include blood type and composition of genetic materials. More specifically, in the latter instance, the step of isolating includes the steps of separating out and determining the composition of genetic material from cells of the individual to be identified, the step of comparing including the comparison of that separated-out genetic material with material from cellular bodies in an frozen umbilical cord segment. This method is essentially set forth in the aforementioned U.S. Pat. Nos. 4,772,549 and 4,861,708 to Philippe M. Frossard.

It is contemplated in accordance with the present invention that as further techniques become developed and known techniques perfected for isolating, identifying and replicating molecular, cellular and other components of umbilical cords, the preserved umbilical cord segments may be taken out of storage and analyzed by the new techniques. Upon determination of the value of a plurality of such biochemical or histological parameters, those values, properly encoded, are stored in a computer together with the personal history and other information recorded at the birth of the respective individual from which the umbilical cord segment was severed and subsequently preserved. As stated above, the personal history information includes statistics pertaining to the individual and the individual's birth, together with an identification of the preserved umbilical cord segment.

Although the invention has been described in terms of particular embodiments and applications, one of ordinary skill in the art, in light of this teaching, can generate additional embodiments and modifications without departing from the spirit of or exceeding the scope of the claimed invention. For example, although a storage apparatus as particularly described herein utilizes liquid nitrogen and/or nitrogen vapor for maintaining the storage chamber at cryogenic temperatures, the principles of the instant invention, such as automatic retrieval and insertion of specimen-containing ampules, computer tracking, and bar code verification, can be used in refrigeration units which operate at more conventional temperatures or in storage units operating at elevated temperatures. In addition, the principle of the bar code verification device, namely, automatic identification of the ampules as they are being retrieved from a storage apparatus, may be implemented with readers other than laser scanners and identification labels other than bar codes. For example, reading may be implemented magnetically, acoustically or photographically. Furthermore, the printer to which the local computers or microprocessors are connected may be used to produce hard copies of umbilical cord data (umbilification information) independently of whether the corresponding umbilical cord segment(s) is being maintained in storage or has been taken out of storage. Alternatively or additionally, the umbilical cord data may be transmitted electronically to the remote computer (CCM) or to other local computers or microprocessors for display on terminal screens or print out at those locations.

Accordingly, it is to be understood that the drawings and descriptions herein are preferred by way of example to facilitate comprehension of the invention and should not be construed to limit the scope thereof.

What is claimed is:

1. A storage apparatus comprising:
    housing means for defining a storage chamber, said housing having an access door;
    means operatively connected to said door for alternately opening and closing same;
    holder means in said chamber for supporting a plurality of specimen-containing receptacles;
    conveyor means for moving said holder means, together with said plurality of receptacles, in said chamber along a path including a snaking portion, said snaking portion having a plurality of vertically extending folds, said path including a segment juxtaposed to said door, said conveyor means including a pair of flexible endless elements extending along said path, said holder means including a plurality of bar members pivotably connected to and extending between said endless elements;
    tracking means operatively connected to said conveyor means for automatically tracking the positions of said plurality of receptacles during motion thereof along said path under action of said conveyor means;
    extraction means disposed outside of said housing means at said door for removing a selectable one of said receptacles positioned in said chamber in juxtaposition to said door;
    selection means outside of said housing means for enabling a selection of one of said receptacles by an operator; and
    control means operatively connected to said selection means, said tracking means, said mean, said conveyor means and said extraction means for operating said conveyor means, upon selection of a given one of said receptacles via said selection means, to move said given one of said receptacles along said path to said door, for operating said mean to open said door, for operating said extraction means to remove said given one of said receptacles from said holder means and out through the opened door.

2. The apparatus defined in claim 1 wherein said control means comprises a computer.

3. A storage apparatus comprising:
    housing means for defining a storage chamber, said housing means having an access door;
    holder means in said chamber for supporting a plurality of specimens;
    conveyor means for moving said holder means, together with said plurality of specimens, in said chamber along a predetermined path including a segment juxtaposed to said door;
    tracking means operatively connected to said conveyor means for automatically tracking the position of each of said specimens during motion thereof along said path under action of said conveyor means; and
    extraction means disposed outside of said housing means at said door for removing a selectable one of said specimens positioned in said chamber in juxtaposition to said door by said conveyor means.

4. The apparatus defined in claim 3 wherein said path includes a snaking portion with a plurality of folds.

5. The apparatus defined in claim 3 wherein said extraction means includes:
    a carriage member movably mounted to said housing means;
    first drive means for moving said carriage member relative to said door;
    holding means for securing a hold on a selected one of said specimens positioned in said chamber in juxtaposition to said door;
    second drive means connected to said holding means for moving said holding means relative to said carriage member and through said door.

6. The apparatus defined in claim 5 wherein said extraction means further includes (a) a housing portion rotatably mounted to said carriage member, said second drive means being at least partially mounted to said housing, and (b) rotary mean operatively connected to said housing portion for rotating same relative to said carriage member.

7. The apparatus defined in claim 3, further comprising:

selection means outside of said housing means for enabling a selection of one of said specimens by an operator; and control means operatively connected to said selection means, said tracking means, said conveyor means and said extraction means for operating said conveyor means, upon selection of a given one of said specimens via said selection means, to move said given one of said specimens along said path to said door, for operating said extraction means to remove said given one of said specimens from said holder means and out through the door.

8. The apparatus defined in claim 7 wherein said control means comprises a computer.

9. A storage apparatus comprising:
housing means for defining a storage chamber, said housing means having an access door;
holder means in said chamber for supporting a plurality of specimens;
an enclosure outside of said housing means;
extraction means disposed outside of said housing means at said door for removing a selectable one of said specimens positioned in said chamber in juxtaposition to said door and inserting the removed one of said specimens into said enclosure; and
treatment means operatively connected to said enclosure for adapting to ambient conditions said removed one of said specimens upon placement thereof into said enclosure by said extraction means.

10. The apparatus defined in claim 9 wherein said enclosure is attached to said housing means.

11. A storage apparatus comprising:
housing means for defining a storage chamber, said housing means having an access door;
holder means in said chamber for supporting a plurality of specimens;
extraction means disposed outside of said housing means at said door for removing a selectable one of said specimens positioned in said chamber in juxtaposition to said door.

12. The apparatus defined in claim 11 wherein said verification means includes a laser reader for scanning bar codes attached to said receptacles.

13. A storage apparatus comprising:
housing means defining a storage chamber;
holder means disposed in said chamber for supporting specimens in said chamber;
conveyor means disposed in said chamber and connected to said holder means for moving specimens in said chamber;
insertion and removal means operatively connected to said housing means for alternately inserting and removing specimens from said chamber; and
control means operatively connected to said insertion and removal means for automatically tracking the locations of specimens in said housing means and for controlling the insertion and removal of specimens from said chamber.

14. The apparatus defined in claim 13 wherein said housing means has an access door, further comprising means operatively connected to said door for alternately opening and closing same, said insertion and removal means including extraction means disposed outside of said housing means at said door for removing a selectable one of said
holder means in said chamber for supporting a plurality of specimens;
conveyor means for moving said holder means, together with said plurality of specimens, in said chamber along a predetermined path including a segment juxtaposed to said door; and
extraction means disposed outside of said housing means at said door for removing a selectable one of said specimens positioned in said chamber in juxtaposition to said door by said conveyor means.

15. The apparatus defined in claim 13 wherein said conveyor means moves said specimens along a predetermined path, said path including a snaking portion with a plurality of vertically extending folds, said path including a segment juxtaposed to said door.

16. The apparatus defined in claim 13, further comprising means operatively connectable to said housing means and said conveyor means for removing all of said specimens in a single operation from said chamber into another storage apparatus.

17. The apparatus defined in claim 13, further comprising selection means operatively connected to said control means and disposed outside of said housing means for enabling a selection of one of said specimens by an operator.

18. The apparatus defined in claim 13 wherein said conveyor means includes transfer means within said storage unit for changing the relative locations of said specimens.

19. The apparatus defined in claim 18 wherein said control means is operatively connected to said transfer means for relocating said specimens according to the type of specimen.

20. The apparatus defined in claim 13, further comprising output means operatively connected to said control means for providing information from said control means regarding said specimens in a format understandable by a human operator.

21. The apparatus defined in claim 13, further comprising marking means in said housing means for marking said specimens, or receptacles containing said specimens, with encoded information.

22. A storage system comprising:
a plurality of storage facilities, each said storage facility including:
housing means defining a storage chamber;
insertion and removal means operatively connected to said housing means for alternately inserting and removing specimen-containing receptacles from said chamber;
local control means at the same location as said housing means and operatively connected to said insertion and removal means for automatically tracking the locations of specimen-containing receptacles in said housing means and for controlling the insertion and removal of specimen-containing receptacles from said chamber; and
remote control means operatively connected to the local control means of each of said storage facilities for monitoring the operations thereof and for cross-checking identities of duplicate specimen-containing receptacles in different ones of said storage facilities.

23. The system defined in claim 22 wherein each of said storage facilities further includes verification means at the respective housing means for automatically verifying that the correct receptacle has been retrieved under the control of the respective local control means, said remote control means having means connected to the local control means of each of said storage facilities for receiving verification of a retrieved receptacle and for comparing identities of receptacles retrieved substantially simultaneously at different ones of said storage facilities.

24. The system defined in claim 23 wherein said verification means includes a laser reader for scanning bar codes attached to the receptacles.

25. A storage system comprising:
a pair of storage facilities, each said storage facility including:
housing means defining a storage chamber;
insertion and removal means operatively connected to said housing means for alternately inserting and removing specimen-containing receptacles from said chamber;
local control means at the same location as said housing means and operatively connected to said insertion and removal means for automatically tracking the locations of specimen-containing receptacles in said housing means and for controlling the insertion and removal of specimen-containing receptacles from said chamber; and
receptacle transfer means operatively connected to the housing means of each of said storage facilities and to the conveyor means of each of said storage facilities for removing all of the specimen-containing receptacles in a single operation from the storage chamber of one of said storage facilities into the storage chamber of the other of said storage facilities.

26. The system defined in claim 25 wherein each of said storage facilities further comprises holder means in said chamber for supporting a plurality of specimen-containing receptacles and conveyor means for moving said holder means, together with said plurality of receptacles, in said chamber along a predetermined path.

27. An apparatus for transferring specimen-containing receptacles from a first storage unit to a second storage unit, wherein each of the storage units includes a respective housing and specimen conveyor means in said housing for holding a multiplicity of said specimen-containing receptacles and moving said receptacles within said housing, said apparatus for transferring comprising:
a transfer housing;
closure means for connecting said transfer housing to the housing of each of the storage units so that said transfer housing communicates in an essentially air tight manner with the housing of each of said storage units;
transfer conveyor means operatively connectable to the specimen conveyor means of each of said storage units for moving predetermined receptacles from one of said storage units to the other of said storage units; and
means operatively connected to said transfer conveyor means for operating same to move said predetermined receptacles from said one of said storage units to said other of said storage units.

28. An apparatus for transferring specimen-containing receptacles from a first storage unit to a second storage unit, wherein each of the storage units includes a respective housing and specimen conveyor means in said housing for holding a multiplicity of said specimen-containing receptacles and moving said receptacles within said housing, said apparatus for transferring comprising:
a transfer housing;
closure means for connecting said transfer housing to the housing of each of the storage units alternately, so that said transfer housing communicates in an essentially air tight manner alternately with the housing of each of said storage units;
transfer conveyor means operatively connectable alternately to the specimen conveyor means of each of said storage units for moving predetermined receptacles initially from one of said storage units and subsequently to the other of said storage units; and
means operatively connected to said transfer conveyor means for operating same to move said predetermined receptacles from said one of said storage units in said transfer housing and subsequently from said transfer housing into said other of said storage units.

29. A storage apparatus comprising:
housing means for defining a storage chamber, said housing means having an access door;
holder means for supporting a plurality of specimens in said chamber;
conveyor means at least partially disposed inside said housing and operatively connected to said holder means for moving a selectable one of said specimens to said door;
extraction means disposed outside of said housing means at said door for automatically removing said one of said specimens positioned in said chamber in juxtaposition to said door; and
selection means outside of said housing means for enabling a selection of one of said specimens by an operator.

* * * * *

UNITED STATES PATENT AND TRADEMARK OFFICE
CERTIFICATE OF CORRECTION

PATENT NO. : 5,125,240
DATED : June 30, 1992
INVENTOR(S) : Hermann Knippscheer and Daniel D. Richard It is certified that error appears in the above-identified patent and that said Letters Patent is hereby corrected as shown below:

Column 1, line 32, change "sample" to --samples--.

Column 3, line 9, change "an" to --and--; line 66, change "on" (second occurrence) to --one--.

Column 4, line 8, change "mean" to --means--.

Column 5, line 58, change "a" to --1--.

Column 7, line 11, change "re" to --are--.

Column 8, line 4, insert --CCl-- after "Computer".

Column 9, line 37, change "ma" to --may--.

Column 10, line 2, insert --along-- after "29".

Column 12, line 15, change "includes" to --including--.

Column 13, line 32, change "on" to --one--.

Column 14, line 1, change "encode" to --encoded--; line 4, change "a" to --an--.

UNITED STATES PATENT AND TRADEMARK OFFICE
CERTIFICATE OF CORRECTION

PATENT NO. : 5,125,240
DATED : June 30, 1992
INVENTOR(S) : Hermann Knippscheer and Daniel D. Richard It is certified that error appears in the above-identified patent and that said Letters Patent is hereby corrected as shown below:

Column 17, line 25, change "the" (second occurrence) to --then--; line 28, change "unbilification" to --umbilification--.

Column 18, line 65, change "an" to --a--.

Column 20,

Claim 1, line 31, change "said mean" to --said means for alternately opening and closing--; line 36, change "said mean" to --said means for alternately opening and closing--.

Claim 6, line 5, change "mean" to --means--.

Column 11,
Claim 11, line 8, change "in juxta-" to --through--; line 9 delete "position to" and change "." (period) to --; and--; after line 9 insert the following subparagraph: --verification means at said door for automatically verifying that the correct specimen has been retrieved by said extraction means.--.
Column 21, Claim 14, delete lines 8-15; line 16, delete "said" (first occurrence); line 17, delete "by said conveyor means".

Signed and Sealed this

Seventh Day of December, 1993

BRUCE LEHMAN

*Attest:*

*Attesting Officer*     Commissioner of Patents and Trademarks